US008183230B2

(12) United States Patent
Adami et al.

(10) Patent No.: US 8,183,230 B2
(45) Date of Patent: May 22, 2012

(54) ANTIMICROBIAL PRESERVATIVES TO ACHIEVE MULTI-DOSE FORMULATION USING BETA-CYCLODEXTRINS FOR LIQUID DOSAGE FORMS

(75) Inventors: Roger C. Adami, Snohomish, WA (US); Frederick David, Sandwich (GB); Julia Ann Wood, Sprague, CT (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 730 days.

(21) Appl. No.: 10/588,070

(22) PCT Filed: Jan. 17, 2005

(86) PCT No.: PCT/IB2005/000100
§ 371 (c)(1),
(2), (4) Date: Dec. 13, 2006

(87) PCT Pub. No.: WO2005/082416
PCT Pub. Date: Sep. 9, 2005

(65) Prior Publication Data
US 2007/0155697 A1     Jul. 5, 2007

Related U.S. Application Data

(60) Provisional application No. 60/540,897, filed on Jan. 30, 2004.

(51) Int. Cl.
*A01N 43/04* (2006.01)
(52) U.S. Cl. .......................................... 514/58; 514/305
(58) Field of Classification Search .................. 514/305, 514/58
See application file for complete search history.

(56) References Cited

U.S. PATENT DOCUMENTS

| | | | |
|---|---|---|---|
| 5,393,762 A | 2/1995 | Desai | |
| 5,807,867 A | 9/1998 | Ito | |
| 5,886,009 A | 3/1999 | Ito | |
| 5,939,433 A | 8/1999 | Ito | |
| 6,222,038 B1 | 4/2001 | Ito | |
| 6,255,320 B1 | 7/2001 | Quallich | |
| 6,861,526 B2 | 3/2005 | Seemayer | |
| 7,163,681 B2 * | 1/2007 | Giles-Komar et al. | .... 424/144.1 |
| 2003/0139443 A1 * | 7/2003 | Bronk et al. | .................. 514/305 |

FOREIGN PATENT DOCUMENTS

| | | |
|---|---|---|
| CA | 2 483 774 | 12/2003 |
| CA | 2 490 735 | 12/2003 |
| EP | 0119737 | 9/1984 |
| JP | 59-152320 | 8/1984 |
| WO | WO00/12137 | 3/2000 |
| WO | WO01/01955 | 1/2001 |
| WO | WO03/009848 | 2/2003 |
| WO | WO03/072141 | 4/2003 |
| WO | WO03/080079 | 10/2003 |
| WO | WO2005/075473 | 8/2005 |
| WO | WO2005/082366 | 9/2005 |
| WO | WO2005/082419 | 9/2005 |

OTHER PUBLICATIONS

Ono et al. Determination of stability constant of β-cyclodextrin complexes using the membrane permeation technique and the permeation behavior of drug-competing agent—β-cyclodextrin ternary systems, European Journal of Pharmaceutical Sciences, vol. 8 pp. 133-139, 1999.*

(Continued)

*Primary Examiner* — Jeffrey S. Lundgren
*Assistant Examiner* — Ibrahim D Bori
(74) *Attorney, Agent, or Firm* — Paul M. Misiak

(57) ABSTRACT

The present invention is directed to pharmaceutical compositions containing a therapeutically effective amount of an Active Pharmaceutical Ingredient ("API"), a pharmaceutically acceptable cyclodextrin and a pharmaceutically acceptable preservative. The invention is also directed to pharmaceutical compositions of the compounds of Formula (I) wherein $R^2$ is selected from the group consisting of methyl, ethyl, isopropyl, sec-butyl and tert-butyl and a pharmaceutically acceptable cyclodextrin and preservative. Formula (I): In particular, the invention is directed to pharmaceutical compositions of the compound of Formula 1a, and a pharmaceutically acceptable cyclodextrin and a preservative.

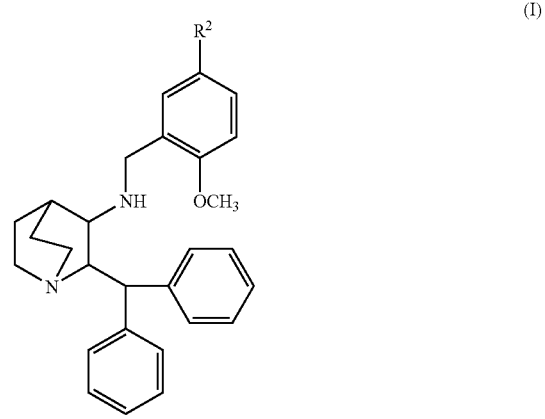

(I)

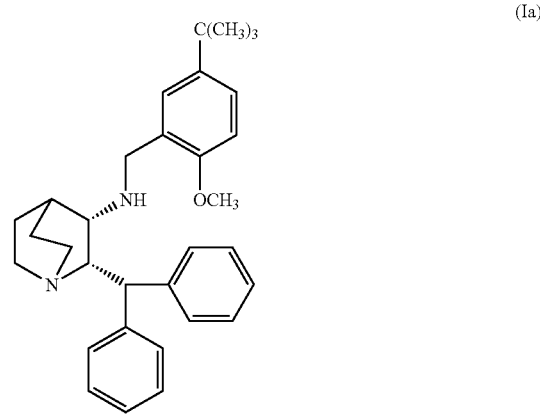

(Ia)

7 Claims, 4 Drawing Sheets

OTHER PUBLICATIONS

Hesketh et al., Randomized Phase II Study of the Neurokinin 1 receptor Antagonist CJ-11,974 in the Control of Cisplatin-Induced Emesis, Jan. 1999, Journal of Clinical Oncology vol. 17, No. 1 pp. 338-343.*

Lehner S J et al, J of Pharm. and Pharmacol., "Effect of Hydroxypropyl-B-cylodextrin on the Antimicrobial Action of Preservatives," vol. 46, pp. 186-191, 1994.

* cited by examiner

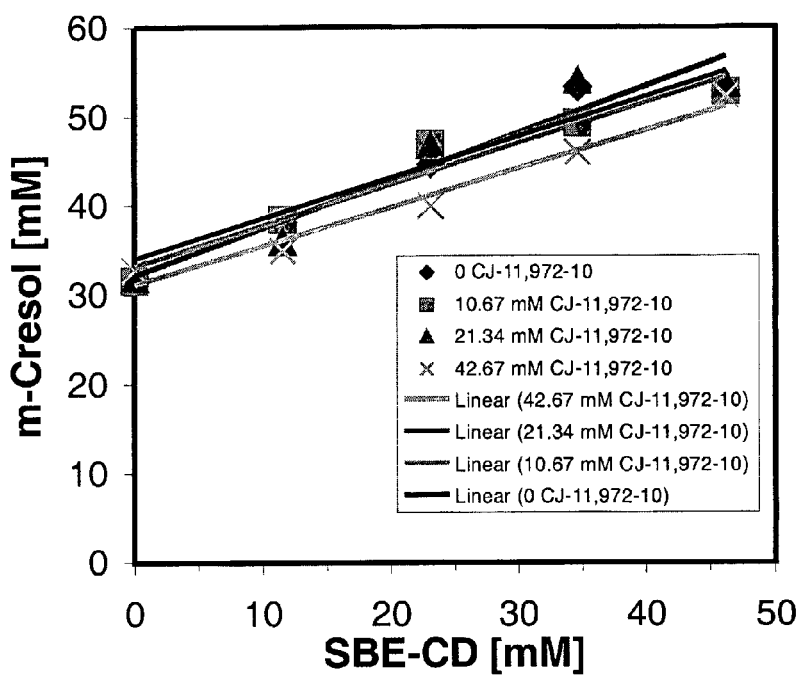
Figure 1: Saturated meta-cresol solutions were prepared in varying amounts of SBE-CD and drug. The samples were filtered and the concentration of preservative in solution was measured. Meta-cresol concentration showed linear increase as SBE-CD was increased. The concentration of drug did not significantly alter the solubility of m-cresol in SBE-CD.

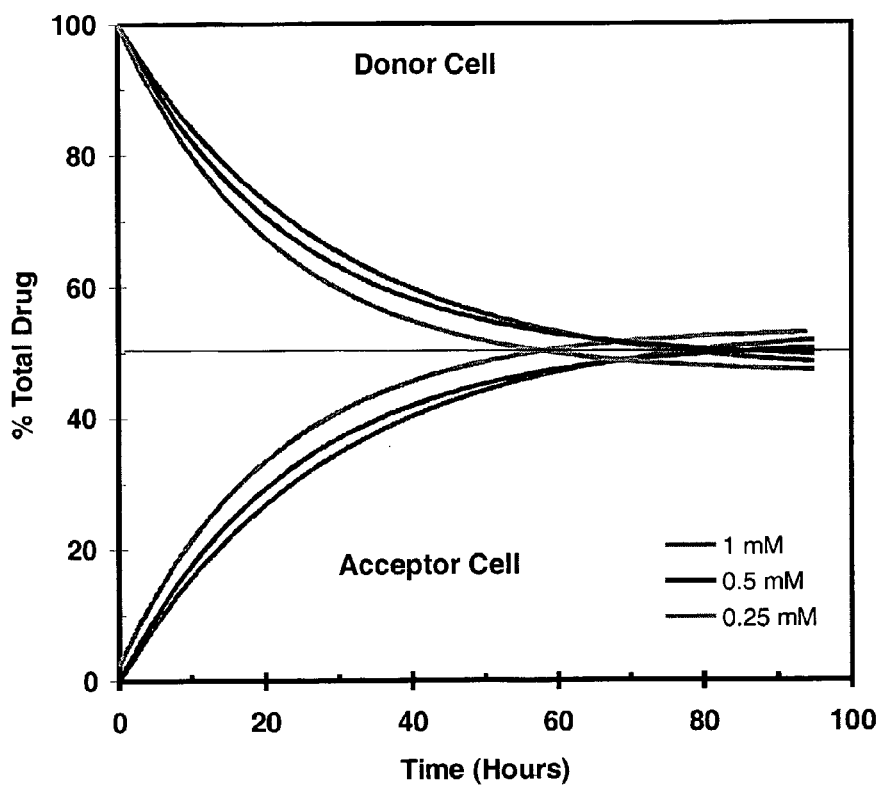
Figure 2: Compound of Formula Ia concentration vs. time at 1, 0.5, and 0.25mM compound of Formula Ia, fit to Equation 11 using Scientist software. Compound of Formula Ia was loaded to the donor side of the dialysis cell. The concentration of drug in the donor and accepter side is presented against time. The drug reaches equilibrium in ~48 hours.

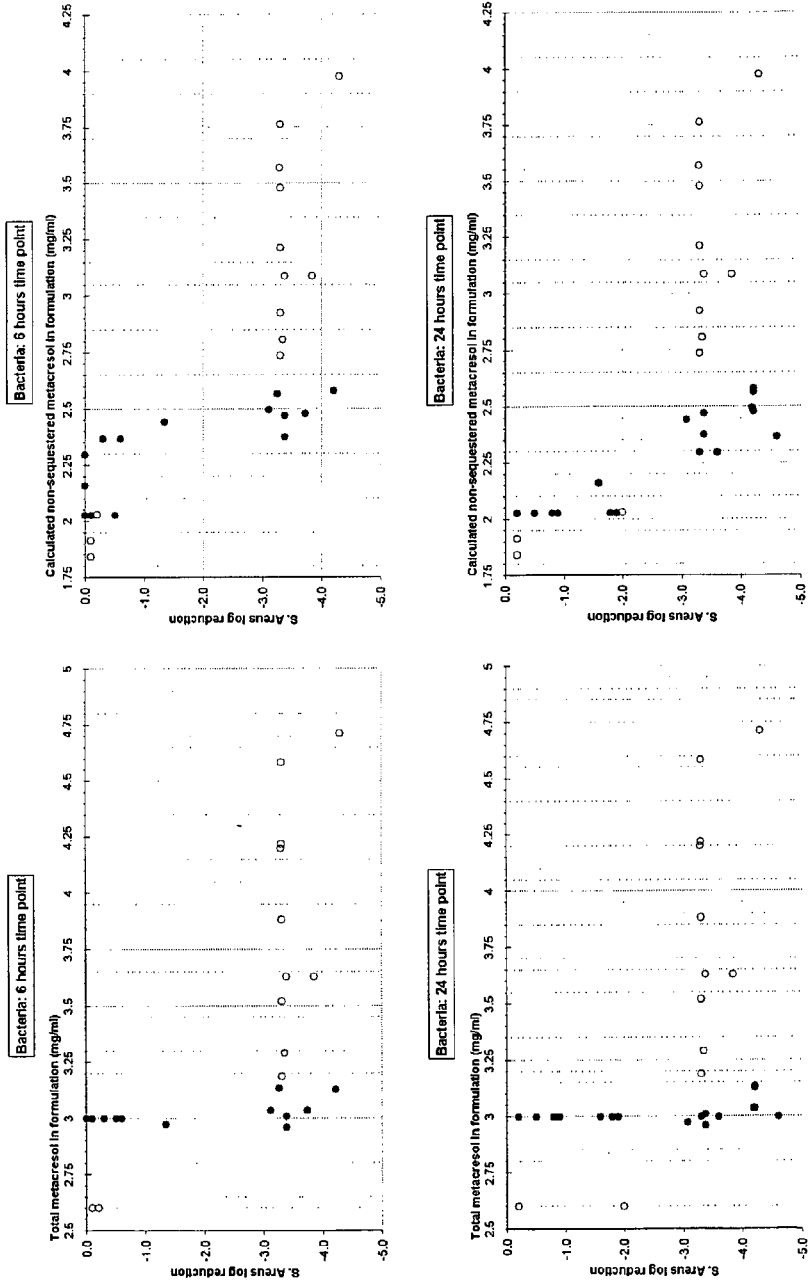
Figure 3: comparison between bacterial efficacy as a function total quantity of metacresol and as a function of calculated sequestered metacresol for S. Aureus at 6h and 24h time points. The full circles are data corresponding to formulations containing a total of 2.95 to 3.15 mg/mL meta-cresol.

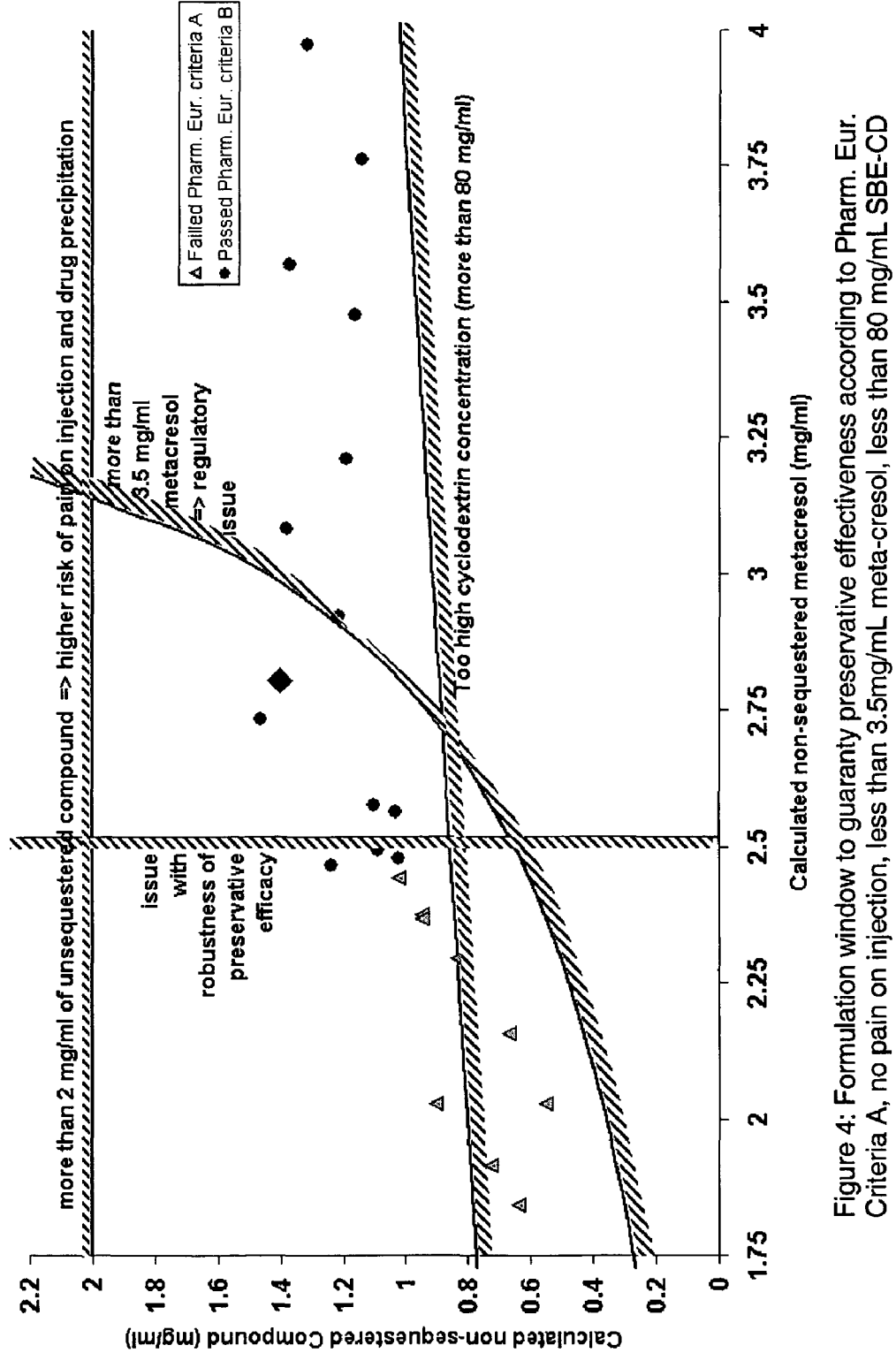
Figure 4: Formulation window to guaranty preservative effectiveness according to Pharm. Eur. Criteria A, no pain on injection, less than 3.5mg/mL meta-cresol, less than 80 mg/mL SBE-CD

ANTIMICROBIAL PRESERVATIVES TO ACHIEVE MULTI-DOSE FORMULATION USING BETA-CYCLODEXTRINS FOR LIQUID DOSAGE FORMS

CROSS-REFERENCE TO RELATED APPLICATIONS

This application is the national phase of international application PCT/1132005/000100, filed Jan. 17, 2005, which claims the benefit of U.S. Provisional Patent Application 60/540,897, filed Jan. 30, 2004, hereby incorporated by reference in its entirety.

FIELD OF INVENTION

The present invention is directed to pharmaceutical compositions containing a therapeutically effective amount of an Active Pharmaceutical Ingredient ("API"), a pharmaceutically acceptable cyclodextrin and a pharmaceutically acceptable preservative. The invention is also directed to pharmaceutical compositions of the compounds of Formula I, wherein $R^2$ is selected from the group consisting of methyl, ethyl, isopropyl, sec-butyl and tert-butyl and a pharmaceutically acceptable cyclodextrin and preservative.

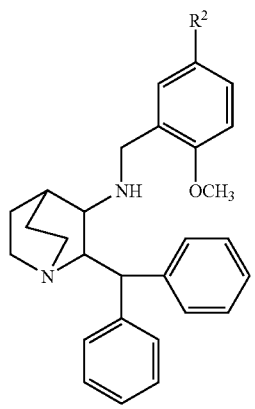

I

In particular, the invention is directed to pharmaceutical compositions of the compound of Formula Ia, and a pharmaceutically acceptable cyclodextrin and a preservative.

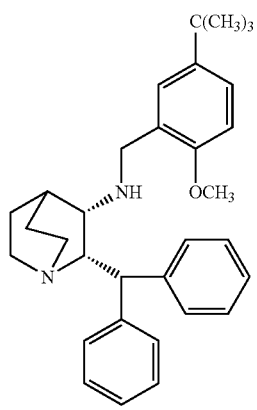

Ia

The invention is further directed to improving injection site toleration of injectable aqueous solutions comprising the compound of Formula I, or its pharmaceutically acceptable salts, a β-cyclodextrin and a preservative.

The invention is also directed to a method of developing a preserved API composition.

BACKGROUND OF INVENTION

Administering neurokinin receptor antagonists, including the compounds of Formula I and Ia, present various problems with regard to injection site tolerance (e.g., irritability of subject, irritation, inflammation, swelling, and/or redness of the site). Although there have been numerous studies with regard to improving injection site tolerance through the use of various substances, none of these studies, however, have focused on neurokinin receptor antagonist administration.

The compounds of Formula I or Ia are the subject of U.S. Pat. Nos. 5,807,867, 6,222,038 and 6,255,320. The preparation of compounds of Formula I and Ia are described therein. The compound of Ia may also be prepared as described in the co-pending U.S. provisional application No. 60/541,323, commonly owned and assigned to Pfizer, Inc. U.S. Pat. No. 5,393,762 also describes pharmaceutical compositions and treatment of emesis using NK-1 receptor antagonists. Co-pending U.S. provisional application No. 60/540,697, commonly owned and assigned to Pfizer, Inc., describes a method of improving anesthesia recovery in patients by administering the compound of Formula I or Ia. The text of the aforementioned applications, patents and all other references cited in this specification are hereby incorporated by reference in their entirety.

The compound of Formula Ia is a basic drug with two amine functional groups, a secondary amine with a pKa of 4.43 and a tertiary amine with a pKa of 9.31. The citrate salt of the compound of Formula Ia has a solubility of 2.7 mg/mL at a pH of 4.2 in 0.02 M phosphate/0.02 M acetate buffered solution. The desired 10 mgA/mL solubility could be obtained by the addition of salts (e.g. NaCl, $CaCl_2$ or sodium acetate), using a partially-aqueous, oleaginous, or micellar vehicle, or adding a modified, parenterally acceptable cyclodextrin. Generally, however, it was observed that formulations containing cyclodextrins provided improved injection site toleration over other approaches to increasing solubility.

Assuring adequate solubility of a pharmaceutical drug in parenteral formulations is crucial, especially when the drug has low aqueous solubility. pH modification of the solution, drug salt form selection, and the use of co-solvents are common approaches used to achieve adequate solubility. A typical approaches involve excipients, such as complexation agents.

Cyclodextrin may enhance solubility by forming an inclusion complex with the drug molecule whereby the insoluble/hydrophobic drug is inserted into the hydrophobic cavity of the cyclodextrin. The outer hydrophilic shell of the cyclodextrin molecule then enhances solubility of the entire complex. Standard terminology for cyclodextrin complexation identifies the cyclodextrin as a "host" molecule and the drug as a "guest" molecule. Unfortunately, the cyclodextrin used to form the inclusion complex may also bind preservatives, inactivating many poorly water-soluble preservatives.

Sulfobutylether-βcyclodextrin (hereinafter "SBE-CD") was found to be effective at both increasing the solubility of compound of Formula Ia and ameliorating injection site reactions. Unfortunately, investigation determined that SBE-CD formed complexes with both antimicrobial preservative (e.g.

meta-cresol) and the compound of Formula Ia, resulting in competitive binding interactions and, in general, antimicrobial ineffectiveness.

Consequently, it was necessary to obtain an optimal balance between a sufficient concentration of cyclodextrin (e.g., SBE-CD) and antimicrobial preservative (e.g. meta-cresol). While a lower concentration of SBE-CD would increase antimicrobial preservative efficacy, this advantage would be offset, however, by a decrease in acceptable injection site toleration ("IST"). These competing performance characteristics necessitated balancing antimicrobial preservative efficacy (criteria A) and acceptable injection-site-toleration for the product.

Co-pending U.S. provisional application No. 60/540,644, contemporaneously filed with the present application and assigned to and owned by Pfizer Inc., describes a method of improving injection site toleration during the parenteral administration of a composition containing the compound of Formula I and cyclodextrin. A cyclodextrin-compatible preservative was also identified, providing desirable multi-use dosing options. Preferably, meta-cresol is used in the formulation to prevent bacterial and fungal development in the formulation during the proposed extended in-use period.

SUMMARY OF INVENTION

In one aspect, the invention is directed to a pharmaceutical composition comprising a therapeutically effective amount of an Active Pharmaceutical Ingredient (API), a β-cyclodextrin, a pharmaceutically acceptable preservative, a pharmaceutically acceptable vehicle, and an optional pharmaceutically acceptable excipient, wherein the preservative demonstrates pharmaceutically acceptable antimicrobial preservative effectiveness.

In a preferred embodiment, the β-cyclodextrin is 2-hydroxypropyl-β-cyclodextrin or sulfobutyl ether-β-cyclodextrin, preferably sulfobutyl ether-β-cyclodextrin.

In another embodiment, the pharmaceutically acceptable preservative is selected from thimerosal, propylene glycol, phenol, or meta-cresol or a combination thereof. Preferably the preservative is meta-cresol. Preferably, the concentration of preservative is about 0.1 mg/mL to about 600 mg/mL. Preferably, the preservative is meta-cresol and is in a concentration of about 0.1 mg/mL to about 20 mg/mL.

In a preferred embodiment, the pharmaceutical composition has a pH in the range of about 3 to about 6.

In a preferred embodiment, the preservative has a binding value to the cyclodextrin that is less than a binding value of the API to cyclodextrin. Preferably, the binding value of the API to cyclodextrin is between 500 $M^{-1}$ and 10,000 $M^{-1}$. Preferably, the binding value of the API to cyclodextrin is between 800 $M^{-1}$ and 3,000 $M^{-1}$.

In another embodiment, the Active Pharmaceutical Ingredient has a greater than or equal to two-fold binding constant with cyclodextrin over that of the preservative. In a preferred embodiment, the binding constant is greater than or equal to five-fold. In a more preferred embodiment, the binding constant is greater than or equal to ten-fold.

In a preferred embodiment, about 1 mg/mL to about 5 mg/mL of the preservative, preferably meta-cresol, is unsequestered in the cyclodextrin. Preferably, about 2.5 mg/mL of the preservative, preferably meta-cresol, is unsequestered in the cyclodextrin.

In a preferred embodiment, the pharmaceutical composition has an antimicrobial effectiveness against bacteria such that the bacteria concentration decreases at a 2 or greater log reduction after 6 hours, a 3 or greater log reduction after 24 hours, and zero recovery of bacteria after 28 days. Preferably, the bacteria are selected from *Escherichia coli* (bacteria, gram negative)(ATCC8739), *Pseudomonas aeruginosa* (bacteria, gram negative)(ATCC9027) or *Staphylococcus auereus* (bacteria, gram positive)(ATCC6538).

In a preferred embodiment, the pharmaceutical composition has an antimicrobial effectiveness against a fungus or mold such that the fungus or mold concentration decreases at a 2 or greater log reduction after 7 days, a 1 log reduction after 14 days, and no increase in fungus or mold after 14 days to about 28 days. Preferably, the fungus is *Candida albicans* (fungus)(ATCC 10231) and the mold is *Aspergillus niger* (mold)(ATCC 16404).

In a preferred embodiment, the pharmaceutical composition has an antimicrobial effectiveness that satisfies Pharmaceopia Europa Criteria A and B and USP AET criteria.

In another aspect, the invention is directed to a pharmaceutical composition comprising a compound of Formula I as Active Pharmaceutical Ingredient,

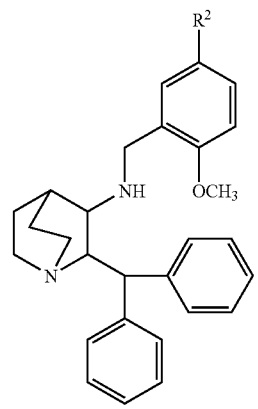

I or its pharmaceutically acceptable salts, wherein $R^2$ is selected from the group consisting of methyl, ethyl, isopropyl, secbutyl and tertbutyl, preferably tert-butyl, a pharmaceutically acceptable β-cyclodextrin, a pharmaceutically acceptable preservative, a pharmaceutically acceptable vehicle and an optional pharmaceutically acceptable excipient.

Preferably, the β-cyclodextrin is 2-hydroxypropyl-β-cyclodextrin or sulfobutyl ether-β-cyclodextrin, preferably sulfobutyl ether-β-cyclodextrin.

Preferably, the pharmaceutically acceptable preservative is selected from thimerosal, propylene glycol, phenol, or meta-cresol, or a combination thereof. Preferably, the preservative is meta-cresol.

Preferably, the pharmaceutical composition has a pH in a range of about 4 to about 5.

In a preferred embodiment, about 1 mg/mL to about 5 mg/mL of the preservative, e.g. meta-cresol, is unsequestered in the cyclodextrin.

In a preferred embodiment, the compound of Formula I, or a pharmaceutically acceptable salt thereof, is in an amount of about 0.1 mg/mL to about 100 mg/mL and the β-cyclodextrin is in an amount of about 20 mg/mL to about 200 mg/mL and the preservative is meta-cresol. Preferably, the β-cyclodextrin is in the amount of 55 mg/mL to 100 mg/mL and the meta-cresol is an amount of about 2.5 mg/mL to 3.5 mg/mL.

In a preferred embodiment, the compound of Formula I is the compound of Formula Ia,

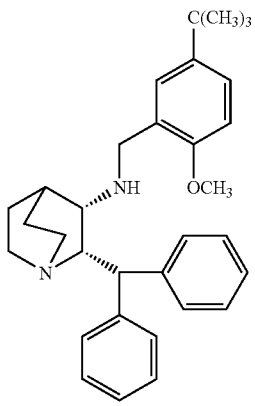

or its pharmaceutically acceptable salts.

Preferably, the compound of Formula Ia, or a pharmaceutically acceptable salt thereof, is in an amount of about 0.1 mg/mL to about 100 mg/mL and the β-cyclodextrin is in an amount of about 20 mg/mL to about 200 mg/mL and the preservative is meta-cresol and is in an amount of about 1 mg/mL to about 5 mg/mL. Preferably, the β-cyclodextrin is in an amount of about 55 mg/mL to about 100 mg/mL and the preservative is meta-cresol and is in an amount of about 2.5 mg/mL to about 3.5 mg/mL. Preferably, the β-cyclodextrin is sulfobutyl ether-β-cyclodextrin.

In a third aspect, the invention is directed to a pharmaceutical composition comprising the compound of Formula Ia,

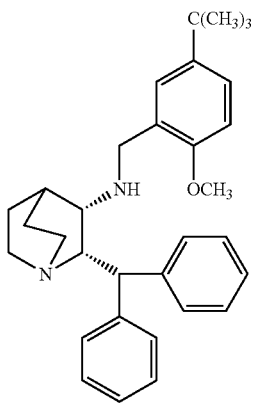

or its pharmaceutically acceptable salts, wherein the compound of Formula Ia is 10 mgA/mL, sulfobutyl ether-β-cyclodextrin is in an amount of about 63 mg/mL and meta-cresol is in an amount of about 3.3 mg/mL, a pharmaceutically acceptable vehicle and an optional pharmaceutically acceptable excipient. Preferably, the pharmaceutically acceptable salt of the compound of Formula Ia is citrate.

In a fourth aspect, the invention is directed to a method for the treatment of emesis or improving anesthesia recovery in mammals comprising parenterally injecting into the mammal an aqueous pharmaceutical composition comprising the above described pharmaceutical compositions of the compounds of Formula I or Ia, the β-cyclodextrin being present in amounts which are sufficient for improved injection toleration at the injection site. Preferably, the pharmaceutically acceptable salt is citrate. Preferably, the composition is administered subcutaneously.

In a fifth aspect, the invention is directed to a method of improving injection site toleration during the treatment of emesis or the treatment of improving anesthesia recovery in a mammal comprising parenterally injecting into the mammal a pharmaceutically acceptable solution of the above described pharmaceutical compositions of the compounds of Formula I or Ia. Preferably, the pharmaceutically acceptable salt is citrate. Preferably, the composition is administered subcutaneously.

In a sixth aspect, the invention is directed to a method to develop a preserved API compositions comprising a therapeutically effective amount of an API, a β-cyclodextrin and a pharmaceutically acceptable preservative.

In a preferred embodiment, the preservative has a binding value to the cyclodextrin that is less than a binding value of the API to cyclodextrin. Preferably, the preservative is selected from thimerosal, propylene, glycol, phenol or meta-cresol or a combination thereof.

In a preferred embodiment, the binding value of the API with the cyclodextrin is greater than 50 $M^{-1}$. Preferably, the binding value of the API with the cyclodextrin is between 500 and 10,000 $M^{-1}$. Preferably, the binding value of the API with the cyclodextrin is between 800 and 3,000 $M^{-1}$.

In a preferred embodiment, Antimicrobial Effectiveness Test (AET) requirements meet Pharmaceopia Europa Criteria A and B and USP AET criteria.

In a further aspect, the invention is directed to a pharmaceutical composition, as defined herein, for use as a medicament especially in, when the composition comprises a compound of formula I or Ia, the treatment of a disease for which a neurokinin receptor antagonist, such as an NK-1 receptor antagonist, is indicated.

In a further aspect, the invention is directed to the use of a pharmaceutical composition, as defined herein, comprising a compound of formula I or Ia, in the manufacture of a medicament for the treatment of a disease for which a neurokinin receptor antagonist, such as an NK-1 receptor antagonist, is indicated.

In a further aspect, the invention is directed to a method for the treatment of a disease for which a neurokinin receptor antagonist, such as an NK-1 receptor antagonist, is indicated in mammals comprising administering to said mammal a therapeutically effective amount of a pharmaceutical composition as defined herein comprising a compound of formula I or Ia.

DEFINITIONS

The term(s) "compound(s) of Formula I" and "compound of Formula Ia" as used herein, means a compound or compounds of Formula I or Ia, prodrugs thereof and pharmaceutically acceptable salts of the compounds or the prodrugs. The compounds utilized in the present invention may be isolated and used per se or in the form of its pharmaceutically acceptable salt, solvate and/or hydrate.

The term "pharmaceutically acceptable salt" refers to inorganic and organic salts of a compound of the present invention. These salts can be prepared in situ during the final isolation and purification of a compound, or by separately reacting the compound, or prodrug with a suitable organic or inorganic acid and isolating the salt thus formed. Representative salts include the hydrobromide, hydrochloride, hydroiodide, sulfate, bisulfate, nitrate, acetate, trifluoroacetate, oxalate, besylate, palmitate, pamoate, malonate, stearate, laurate, malate, maleate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. See, e.g., Berge, et al., *J. Pharm. Sci.*, 66, 1-19 (1977).

Preferably, the pharmaceutically acceptable salt is citrate. The term "citrate salt," as used herein, refers to the citrate monohydrate salt of the compound of Formula Ia, having a molecular weight of 660.82 and a theoretical potency based on the active ingredient of 709 mg/g.

The term "Active Pharmaceutical Ingredient" or "API," as used herein refers to a pharmaceutical drug substance having therapeutic properties and having the ability to bind or be "sequestered" in cyclodextrin. Preferably, the API has a binding value to cyclodextrin greater than 50 $M^{-1}$. More preferably, the API has a binding value to cyclodextrin between about 800 $M^{-1}$ to about 3,000 $M^{-1}$. Even more preferably, the API has a binding value to cyclodextrin between about 500 $M^{-1}$ to about 10,000 $M^{-1}$. Furthermore, preferably, the API has greater than a two-fold binding constant with cyclodextrin over preservative. More preferably, the API has a greater than 5 fold binding constant with cyclodextrin. Even more preferably, the API has greater than or equal to 10 fold binding constant with cyclodextrin.

The term "active ingredient" or "mgA/mL", as used herein, refers to the free base of the compound of Formula Ia, having a molecular weight of 468.69.

The term "cyclodextrin" refers to a compound including cyclic alpha (1→4) linked D-glucopyranose units. α-cyclodextrin refers to a cyclodextrin with 6 cyclic, linked D-glucopyranose units, β-cyclodextrin has 7 cyclic, linked D-glucopyranose units, and β-cyclodextrin has 8 cyclic, linked D-glucopyranose units. These cyclic, linked D-glucopyranose units define a hydrophobic cavity, and cyclodextrins are known to form inclusion compounds with other organic molecules, with salts, and with halogens either in the solid state or in aqueous solutions.

Cyclodextrins vary in structure and properties. For example, the size (e.g. diameter, and depth) and functionality (e.g. hydrophobicity, charge, reactivity and ability to hydrogen bond) of the hydrophobic cavity varies among substituted and unsubstituted α-, β- and γ-cyclodextrins. Typically, a cyclodextrin selected for a formulation has a size and functionality that binds with the target component the other components of the formulation. For the present formulations and methods, it is believed that substituted cyclodextrins, such as hydroxyalkyl cyclodextrins and sulfoalkylether cyclodextrins have a size and functionality that compliment the other components of the formulation. Preferred cyclodextrins include hydroxypropyl-β-cyclodextrin and sulfobutylether-β-cyclodextrin. More preferably, the cyclodextrin is sulfobutylether-β-cyclodextrin ("SBE-CD").

The phrase "therapeutically effective amount" means an amount of a compound of the present invention that (i) treats or prevents the particular disease, condition or disorder, (ii) attenuates, ameliorates or eliminates one or more symptoms of the particular disease, condition or disorder, or (iii) prevents or delays the onset of one or more symptoms of the particular disease, condition or disorder described herein.

The term "mammals" or "animals", as used herein, refers to humans, companion animals such as, but not limited to, dogs, cats and horses, food source animals (e.g., cows, pigs and sheep), zoo animals and other similar animal species.

The phrase "pharmaceutically acceptable" indicates that the substance or composition must be compatible chemically and/or toxicologically, with the other ingredients comprising a formulation, and/or the mammal being treated therewith.

The terms "treating", "treat" or "treatment" embrace both preventative, i.e. prophylactic and palliative treatment.

The term "improved injection site toleration" as used herein means a score of two or less, as defined herein in Table IV.

The term "pharmaceutically acceptable preservative," as used herein, means a preservative. In particular, the formulation containing preservative maintains effectiveness according to the standards set forth in Ph. Eur. $4^{th}$ Ed. 2003 (5.1.3) for parenteral formulations and USP26 NF21S2, <51> for Category 1 pharmaceutical products. Preferably, the preservative has a reduced binding value to cyclodextrin compared to the API, such that the sufficient preservative is "unsequestered" in the cyclodextrin, providing effective antimicrobial effectiveness.

BRIEF DESCRIPTION OF THE DRAWINGS

FIG. 1 depicts the saturated meta-cresol solutions of SBE-CD and compound of Formula Ia. Meta-cresol concentration showed linear increase as SBE-CD was increased. The concentration of drug did not significantly alter the solubility of m-cresol in SBE-CD.

FIG. 2 depicts compound of Formula Ia concentration vs. time at 1, 0.5, and 0.25 mM compound of Formula Ia, fit to Equation 11.

FIG. 3 depicts the comparison between bacterial efficacy as a function of total quantity of meta-cresol and as a function of calculated sequestered meta-cresol for *S. aureus* at 6 hours and 24 hours time points.

FIG. 4 depicts a formulation window to guaranty preservative effectiveness according to Ph. Eur. Criteria A, no pain on injection, less than 3.5 mg/mL meta-cresol, and less than 80 mg/mL SBE-CD.

DESCRIPTION OF INVENTION

Development of parenteral formulations utilizing cyclodextrin for solubilization, or for other purposes, requires an understanding of the interaction between the drug and cyclodextrin. A pharmaceutical drug that is solubilized by cyclodextrin is bound at a stoichiometric relationship related to an inherent binding constant. This relationship varies based on several factors such as the structure of the drug, cyclodextrin, and solution properties (e.g., pH, ionic strength, and cosolvency).

Formulations having multiple excipients further complicate the interaction. For example, in parenteral multi-use formulations containing a preservative, the preservative may compete with the drug for cyclodextrin binding. It was previously reported that 2-hydroxypropyl-β-cyclodextrin interacts not only with drug molecules but can also form complexes with antimicrobial preservatives. Loftsson, T. et al., *Drug Development and Industrial Pharmacy* 1992, 18(13), 1477-1484.

Binding of the preservative and cyclodextrin, however, decreases the antimicrobial effectiveness of the preservative, since the preservative needs to be unbound in solution. A minimum requirement for the efficacy of the preservation for parenteral products is described in the European Pharmacopoeia, criteria A being applicable, and in the U.S. Pharmacopoeia. Antimicrobial Preservatives for proposed formulations were evaluated pursuant to the Antimicrobial Effectiveness Testing ("AET") criteria.

A multi-dose formulation of the compound of Formula Ia containing 10 mgA/mL compound of Formula Ia and 10% (w/v) cyclodextrin at pH 4.4 was utilized to identify an efficacious antimicrobial preservative that did not significantly interact with cyclodextrin. From preliminary experiments, the solubility of the compound of Formula I in the presence of 2-hydroxypropyl-β-cyclodextrin was similar to the solubility in the presence SBE-CD. Furthermore, both yielded a formulation with acceptable injection site toleration ("IST"). In addition to compatibility with cyclodextrin, e.g. SBE-CD, there was additional criteria that limited the antimicrobial preservatives acceptable for the formulation. These criteria were physical and chemical compatibility with compound of Formula Ia; preservative effectiveness against bacteria, molds, and yeasts at pH of about 4.4 and acceptable injection site toleration.

As discussed more fully in the Experimental section, a preliminary screen for an antimicrobial preservative for the multidose compound of Formula Ia formulation was conducted with chlorocresol, phenyl ethanol, benzyl alcohol, ethanol, bronopol, sucrose, chlorhexidine gluconate, thimerosal, benzethonium chloride, benzalkonium chloride, chlorobutanol, benzoic acid, meta-cresol, phenol, and 25% propylene glycol. Initial results indicated that thimerosal, chlorobutanol/phenylethanol, ethanol and propylene glycol (50%) satisfied USP/Ph. Eur. requirements (Table VII).

When considering injection site toleration issues, chlorobutanol/phenylethanol, ethanol and propylene glycol demonstrated poor injection site toleration (Table VIII). Conversely, thimerosal and meta-cresol provided good injection site toleration.

Benzethonium chloride and benzoic acid were both ineffective at reducing the microorganisms after 7 days. Propylene glycol (25%) was active against bacteria only in the presence of SBE-CD, but ineffective against the fungi. On the other hand, the phenolic compounds, phenol and meta-cresol were effective at reducing the microorganisms, but their activity against bacteria was greatly diminished when SBE-CD was present in the formulation.

It was suspected, and determined by the inventors, that the difficulties encountered to preserve the desired formulation were due to an interaction between the antimicrobial preservative (e.g. meta-cresol) and the SBE-CD. In particular, preservative, for example meta-cresol, was likely sequestered by SBE-CD, rendering the meta-cresol inactive against bacteria and fungi. In order to demonstrate this theory, the binding constant of compound of Formula Ia to SBE-CD and meta-cresol to SBE-CD were determined ($K_p$). These constants were used to calculate the concentration of non-sequestered meta-cresol in the formulations tested for anti-microbial efficacy. The average values used for calculations are binding constant for drug ("$K_D$"=1000) and binding constant for preservative ("$K_p$"=28).

In cases where preferential binding of one component is desired, it is desirable to quantify the bound portion of each component at equilibrium. The binding of one component versus another in solution can be measured using techniques such as spectroscopy, or calorimetry. Gadre, A., and Connors, K. A. "Binding of Substituted Acetic Acids to α-Cyclodextrin in Aqueous Solution" J. Pharm. Sci. 1997 86(11):1210-1214). In order to differentiate inclusion binding from other possible solubilization effects of a ternary formulation agent, such as stacking or hydrotropy, a method is required to determine the binding constant of one component bound to cyclodextrin in the presence of other competitive binders. The ability to distinguish between binding and other modes of interaction is significant for understanding and designing optimal formulations.

In the present invention, the method to determine binding constants utilizes equilibrium dialysis in the development of a multi-use parenteral formulation containing SBE-CD and a preservative. In particular, the method was applied in developing a parenteral formulation comprising the compound of Formula Ia, a cyclodextrin (SBE-CD) and a preservative (meta-cresol). This approach is applicable to compounds other than the compound of Formula Ia in developing parenteral formulations and is within the scope of this invention. Development of the formulation using this approach resulted in optimization of cyclodextrin bound drug and unbound preservative. The significance of this procedure is its ability to measure the binding constant of multiple compounds competing for binding with the cyclodextrin. The experimental dialysis data also provides an easily interpreted representation of binding in the formulation by visualizing the degree of interaction by the equilibrium established following dialysis.

Equilibrium dialysis permits calculation of binding constants by modeling the resultant diffusion rate across a semi-permeable membrane with an equilibrium end point. Equilibrium dialysis is performed by allowing the substrate in a solution containing bound substrate and ligand in a donor compartment of an equilibrium dialysis apparatus (cell) to equilibrate over time with an acceptor compartment. Ono, N., Hirayama, F., Arima, H., Uekama, K. "Determination of Stability Constant of β-Cyclodextrin Complexes Using the Membrane Permeation Technique and the Permeation Behavior of Drug Competing Agent-β-Cyclodextrin Ternary Systems" Eur. J. Pharm. Sci. 1999 9:133-139. The acceptor cell contains no ligand. The membrane is semi-permeable allowing the typically low molecular weight substrates to freely diffuse, while the cyclodextrin (MW=2163) remains in the donor compartment. Sampling from both compartments over time yields a time-concentration profile of substrate in both the donor and acceptor compartments of the dialysis cell.

A mathematical model describing the diffusion rate of drug across the membrane can be derived for systems containing two or more components in solution. The dialysis rate and binding constant for the substrates are obtained by resolving the equation using nonlinear curve fitting software. Depending on the interactions between the components it is possible to describe the competitive binding that occurs in the solution. The equilibrium binding constant is a measure of the relative concentration of meta-cresol bound to SBE-CD according to the chemical equilibrium equation below: S=meta-cresol, L=SBE-CD. S:L indicates the complex formed between meta-cresol and SBE-CD.

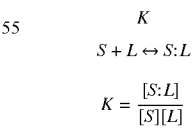

$$S + L \underset{}{\overset{K}{\leftrightarrow}} S{:}L$$

$$K = \frac{[S{:}L]}{[S][L]}$$

Solubility Analysis.

The citrate salt of the compound of Formula Ia has a solubility of 2.7 mg/mL at a pH of 4.2 in 0.02 M phosphate/0.02 M acetate buffered solution. Traditional solubility methods were performed initially to determine the solubility and binding constants of compound of Formula Ia and preservative with SBE-CD. These studies allowed determination of the stoichiometry of binding between SBE-CD and compound of Formula Ia as seen by the linear slope in the molar solubility relationship of compound of Formula Ia and SBE-CD (FIG. 1).

Binding was calculated for meta-cresol using solubility analysis. The experiment was performed at different concentrations of compound of Formula Ia to determine if there was any effect from the presence of drug in solution on the meta-cresol binding constant. Meta-cresol solubility was measured in excess (saturated) meta-cresol and the equilibrium binding constant was calculated using the following equation:

$$S_t = s_0 + \frac{K_{11} s_0 L_t}{1 + K_{11} s_0}$$

Where $S_t$ is the total solubility of meta-cresol, $s_0$ is the inherent solubility of meta-cresol, $L_t$ is the total concentration of SBE-CD (ligand) and $K_{11}$ is the equilibrium binding constant of meta-cresol assuming a 1 to 1 binding stoichiometry.

Applying the solubility method, the equilibrium binding constant of meta-cresol averaged 27.6 $M^{-1}$ across the studies. There was minimal effect on the binding from the presence of compound of Formula Ia as is shown in Table I. This data was used to compare results to the equilibrium dialysis method currently investigated. Compound of Formula Ia had a binding constant of 1040 $M^{-1}$ at pH 4.4.

TABLE I

Calculated binding constants from meta-cresol saturated solubility experiments in varying SBE-CD and drug (compound of Formula Ia). The slope of meta-cresol solubility vs. SBE-CD concentration was used to estimate binding. The addition of compound of Formula Ia did not significantly alter meta-cresol concentration.

| Compound of Formula Ia [mM] | Slope | y-intercept [mM] | $R^2$ | $K_{11}$ (equilibrium) |
|---|---|---|---|---|
| 00.00 | 0.46 | 34.06 | 0.88 | 24.53 |
| 10.67 | 0.46 | 33.15 | 0.95 | 25.78 |
| 21.34 | 0.53 | 32.15 | 0.92 | 35.46 |
| 42.67 | 0.43 | 31.15 | 0.97 | 24.59 |
| Average Binding Constant [$M^{-1}$] | | | | 27.59 |

Equilibrium Dialysis Method

The initial experiments established the equilibrium dialysis flux rates for compound of Formula Ia and meta-cresol across the 500 MWCO dialysis membrane. Three different concentrations of compound of Formula Ia were initially loaded into the donor side of the dialysis well. Samples were withdrawn at various time intervals and concentration of free component was measured using HPLC. Equilibrium was achieved for each tested condition after approximately 4 days. The smoothed line was a fit to the data using the model for a unitary system presented in the discussion. The equilibrium point for all these control experiments was reached after 50% of the total drug was distributed uniformly across the donor and acceptor sides of the well. This asymptotic approach to equilibrium was modeled and the dialysis rates were calculated, Table II.

TABLE II

Calculated binding constants from equilibrium dialysis method. Asymptotic diffusion rates were fit to equation 11 using numerical line-fitting software to generate binding constants.

| Approximate Ratio | Compound of Formula Ia | Meta-cresol [mM] | SBE-CD [mM] | k ($hr^{-1}$) | $K_{eq}$ [$M^{-1}$] |
|---|---|---|---|---|---|
| 1:1 | 1.0 | | 1.0 | 0.015 | 740 |
| 1:2 | 0.5 | | 1.0 | 0.013 | 1092 |
| 1:4 | 0.25 | | 1.0 | 0.012 | 1444 |
| 1:1 | | 1.1 | 1.0 | 1.984 | 88 |
| 1:2 | | 0.6 | 1.0 | 2.182 | 75 |
| 1:4 | | 0.3 | 1.0 | 2.761 | 85 |
| 1:1 | 1.0 | 1.0 | 1.0 | 0.018 | 690 |
| 1:2 | 0.5 | 0.5 | 1.0 | 0.013 | 720 |
| 1:4 | 0.25 | 0.25 | 1.0 | 0.011 | 520 |

The primary method of analyzing the data was to perform calculations from equilibrium dialysis data, as described below. In particular, the rate of diffusion across the membrane was calculated using the following equations:

The rate of diffusion from the donor phase is defined by the following relationship:

$$[D]_t - [D]_{eq} = ([D]_0 - [D]_{eq}) e^{(-2kt)} \qquad (1)$$

Rate of diffusion into the Acceptor Phase:

$$[D]_{eq} - [D]_t = [D]_{eq} e^{(-2kt)} \qquad (2)$$

wherein k=permeation rate constant, $min^{-1}$ $[D]_0$=concentration in donor or acceptor at time 0

$[D]_t$=concentration in donor or acceptor at time t $[D]_{eq}$=concentration in donor or acceptor at equilibrium t=time (min)

The basis of calculation in the presence of SBE-CD is to assume that complexation occurs only in the donor phase according to the standard complexation reaction:

$$D + L \overset{K}{\leftrightarrow} D{:}L$$

$$K = \frac{[D{:}L]}{[D][L]}$$

The differential equation governing the diffusion of drug into the acceptor phase is given below:

$$\frac{d[D]_A}{dt} = k[D]_F - k[D]_A \qquad (3)$$

The mass balance for drug in the system is described below:

$$[D]_{tot} = [D]_F + [D]_A + [D{:}CyD] \qquad (4)$$

where $[D]_F$ and $[D]_A$ are free drug in the donor well and free drug in the acceptor well, respectively. The mass balance for cyclodextrin in the system, maintained within the donor phase, is given below:

$$[CyD]_{tot} = [CyD]_F + [D{:}CyD] \qquad (5)$$

Substituting the complexed drug from the mass balance (eq) into the equilibrium relationship gives:

$$K = \frac{([D]_{tot} - [D]_F - [D]_A)}{[D]_F [CyD]_F} \quad (6)$$

Solving for free drug and substituting into eq. 3 results in:

$$\frac{dD_A}{dt} = k\left[\left(\frac{D_{tot} - D_A}{1 + K \cdot CyD_F}\right) - D_A\right] \quad (7)$$

Simplifying results in:

$$\frac{dD_A}{dt} = k\left[\frac{D_{tot} - (K \cdot CyD_F + 2)D_A}{1 + K \cdot CyD_F}\right] \quad (8)$$

Using the cyclodextrin mass balance and solving for free cyclodextrin in terms of known values gives:

$$CyD_F = CyD_{tot} - D_{tot} + D_F + D_A \quad (9)$$

Replacing free drug, $D_F$, by its equilibrium relationship leads to:

$$CyD_F = CyD_{tot} - D_{tot} + D_A + \frac{D_0 - D_A}{1 + K \cdot CyD_F} \quad (10)$$

Solving the quadratic for free cyclodextrin, $CyD_F$ provides:

$$CyD_F = \frac{-1 + K \cdot D_A - K \cdot D_0 + K \cdot CyD_{tot} \pm \sqrt{4K \cdot CyD_{tot} + (1 - K \cdot D_A + K \cdot D_0 - K \cdot CyD_{tot})^2}}{2 \cdot K} \quad (11)$$

The value for $CyD_F$ may be substituted into equation 8. An implicit solution using equations 8 and 11 allow determination of both the equilibrium binding constant K and the rate of diffusion, k, into the acceptor phase by using the time, concentration date, and the initial conditions.

Sampling removed the higher concentration of drug (e.g. compound of Formula Ia) from the donor side of the dialysis chamber, which resulted in raw data depicting concentrations coming to equilibrium with the midpoint skewed below 50%. This sampling bias was corrected for, and the graphs were normalized to represent a 50% midpoint. This normalization was applied prior to fitting the curves to the model.

The method utilized provided a measured binding constant for drug and SBE-CD. The value obtained from the equilibrium dialysis method was 1092 M−1 (±352 M−1, n=3), compared to 1040 M−1 (n=1) for the solubility method. The binding constant for preservative and SBE-CD, using the solubility method was 28 M−1 (n=1) compared to 83 M−1 (±7 M−1) using equilibrium dialysis. The data demonstrates that, in binary systems, both drug (e.g., compound of Formula Ia) and preservative bind to the cavity in SBE-CD, although in this case the drug binding constant was 13-fold greater than preservative. The data showed that in ternary systems comprised of SBE-CD, drug (e.g., compound of Formula Ia), and preservative, at the ratios tested, the equilibrium profile indicated that the preservative was not bound to cyclodextrin due to competitive binding with the drug.

Based upon the above calculations to obtain the amount of sequestered meta-cresol and compound of Formula Ia, proposed formulations were developed and evaluated for antimicrobial efficacy. FIG. 3 demonstrates no clear relationship between the total meta-cresol concentration contained in the formulation and the log reduction of bacterial population, 6 or 24 hours after spiking a known amount of *Staphylococcus Aureus* (i.e. formulations containing about 3 mg/mL meta-cresol seem to equally have a log reduction as low as 0 or as high as greater than 4.6). When the same data set is plotted against the calculated non-sequestered meta-cresol concentration in the formulation, (FIG. 4) however, a relationship is visible. This data set was produced with a number of formulations containing 9.0 to 11.0 mgA/mL of compound of Formula Ia, 2.5 to 4.75 mg/mL meta-cresol and 60 to 100 mg/mL SBE-CD. The appearance of a plateau at the higher concentrations is only due to the limitation in the bactericidal efficacy measurement method. As the method consists in evaluating the population not killed by the preservative, when the whole population is dead (i.e. none is detectable any more ~100%) the figure quoted is of the form: a log reduction greater than a value usually between 3 and 5.

Another factor was the concentration of non-sequestered compound of Formula Ia, since higher concentrations were demonstrated to create pain on injection. Furthermore, there was risk of precipitation, if the concentration reached the limit of aqueous solubility of compound of Formula Ia at the desired formulation pH of about 4.4. Accordingly, the level of non-sequestered compound of Formula Ia was minimized in an attempt to maintain the concentration below 2 mg/mL.

Two additional parameters were: (1) the level of total meta-cresol concentration; and (2) the level of cyclodextrin (e.g., SBE-CD) should be kept as low as possible and, in particular, below 80 mg/mL to prevent binding to and inactivating meta-cresol. (See FIG. 4). Accordingly, formulations containing 9.0 to 11.0 mgA/mL of compound of Formula I, 2.5 to 4.75 mg/mL meta-cresol and 60 to 100 mg/mL SBE-CD were designed to contain known amount of calculated non-sequestered compound of Formula I and known calculated amount of non-sequestered meta-cresol. The formulations were analyzed for preservative effectiveness. These results are reported in FIG. 4. From these results a limit of confidence in robust preservative effectiveness was defined and reported on FIG. 4.

Based on these results, the preferred formulation containing calculated non-sequestered concentrations of meta-cresol (2.8 mg/mL) and compound of Formula I (1.4 mg/mL), corresponding to the black diamond on FIG. 4, was selected. This formulation corresponded to actual total concentrations of 10 mgA/mL of compound of Formula I, 63 mg/mL SBE-CD and 3.3 mg/mL meta-cresol at pH 4.4.

The principles described above for the development of a pharmaceutical formulation of the citrate salt of compound of Formula Ia are applicable in the development of other parenteral formulations comprising pharmaceutical drugs, cyclodextrin and preservative. In particular concentrations of drug, cyclodextrin and preservative should be adjusted to have minimum concentration of non sequestered preservative (2.1 mg/ml when using metacresol).

Formulation. In general, formulations are prepared by dissolving a therapeutically effective amount of the compound of Formula Ia in an aqueous pharmaceutically acceptable diluent. A pharmaceutically acceptable salt of the compound of Formula I may also be used, such as the citrate or malate salts. A cyclodextrin is added to the solution in a concentration range of about 2% to about 40%. Preferably, the cyclodextrin comprises about 5% to about 20% of the pharmaceutical composition and more preferably about 5% to about 10%. Preferably, the cyclodextrin is a β-cyclodextrin: hydroxypropyl β-cyclodextrin, sulfobutylether β-cyclodextrin or other pharmaceutically acceptable substituted β-cyclodextrin. A preservative is added to the formulation on a weight basis.

As used herein, a "therapeutically effective amount" for a dosage unit may typically about 0.5 mg to about 500 mg of active ingredient. The dose may vary, however, depending on the species, variety, etc. of animal to be treated, the severity and the body weight of the animal. Accordingly, based upon body weight, typical dose ranges of the active ingredient may be from about 0.01 to about 100 mg per kg of body weight of the animal. Preferably, the range is from about 0.10 mg to about 10 mg per kg of body weight, and more preferably, from about 0.2 to about 2 mg per kg of body weight.

For example, A 10 mgA/mL compound of Formula Ia formulation allows the preferred injection volume of 0.5 to 3.0 mL at a 1 mg/kg dose to treat 5 to 30 kg animals, which covers the majority of patients. Use of the product in larger mammals can be accommodated by using a larger syringe or multiple injections. Use of the product in small dogs and cats will require smaller injection volumes.

The veterinary practitioner, or one skilled in the art, will be able to determine the dosage suitable for the particular individual patient, which may vary with the species, age, weight and response of the particular patient. The above dosages are exemplary of the average case. Accordingly, higher or lower dosage ranges may be warranted, depending upon the above factors, and are within the scope of this invention.

Pharmaceutical compositions of the compound of Formula Ia were developed such that a therapeutically effective amount of the compound of Formula Ia could be administered to a patient with an acceptable injection site toleration. Injection site toleration was measured by inspecting the patient for signs of reaction, including erythema (size); skin thickening (size), pain on palpation and edema. Table VI provides a detailed explanation of the scoring system: a score of 0 (no reaction) to 4 (severe reaction) was given for each characteristic and each injection site daily.

The formulation of the citrate salt of the compound of Formula Ia is self-buffered by the citrate counterion (21.3 mM) at the native pH of ca. 4.4. If other pharmaceutically acceptable salts are utilized, however, a pharmaceutically acceptable buffer may be required. The preferred formulation is 10 mgA/mL compound of Formula Ia as the citrate monohydrate salt, about 63 mg/mL SBE-CD, and about 3.3 mg/mL meta-cresol at pH 4.4.

GENERAL EXPERIMENTAL PROCEDURES

A. Equilibrium Dialysis Method for Determining Binding Constants

Materials. Meta-cresol (MW=108.14) was obtained from Aldrich, St. Louis, Mo. A 20-cell equilibrium dialyzer, equipped with 2 mL Teflon cells and 500 MWCO cellulose ester asymetric membranes was used (Spectrum, Rancho Dominguez, Calif.). Compound of 1a (free base=468.69), may be prepared as set forth in section B of Experimental Procedures.

Preparation of Formulations. Three different test formulations were prepared composed of either single component controls; binary systems containing either drug or m-cresol, and SBE-CD; or ternary systems containing drug, m-cresol, and SBE-CD. Formulations were prepared at room temperature at different ratios and concentrations 24 hrs prior to testing to assure equilibrium binding. The formulations were prepared by first dissolving SBE-CD at the appropriate concentration and then adding drug or m-cresol and allowing it to dissolve in the cyclodextrin solution.

Dialysis Method. One mL of complexed or control formulation was loaded in the donor side of the membrane. The acceptor side was loaded with 1-mL of sodium citrate (pH 4.4) to maintain ionic equilibrium across the chamber. At various time points, 50 μL aliquots were removed from both the donor and acceptor sides of the equilibrium dialysis chamber and analyzed using HPLC. The concentration over time profile (mM) of ligand on each side was plotted for each ratio.

HPLC Method. Samples were loaded neat onto an HP 1100 HPLC equipped with an Agilent Eclipse XDB-C8 column. The total run time was 10 minutes. The mobile phase consisted of 25% 25 mM ammonium acetate and 75% methanol Detection was performed using absorbance at 271 nm or fluorescence detection. Peaks were integrated using Turbochrome software [Perkin Elmer\San Jose, Calif.].

Control Experiments. The dialysis rates of compound of Formula Ia and meta-cresol were measured alone across the 500 MWCO membrane. Different concentrations of meta-cresol and compound of Formula Ia were placed on the donor side of the equilibrium dialyzer. The concentrations of corresponding complexation experiments were chosen to match the concentration of drug or preservative in the single component systems.

Binary Systems. These experiments were performed to quantify the binding of either drug or m-cresol with SBE-CD. Three separate mixtures were tested which consisted of: compound of Formula Ia with SBE-CD, meta-cresol with SBE-CD, and drug with meta-cresol. The molar ratios of SBE-CD to drug or preservative were 1:1, 2:1, and 4:1.

Ternary Systems. Several experiments were performed to test the effects of all three formulation components on the dialysis rate of drug and preservative. In these, SBE-CD concentration was fixed while the amounts/ratios of compound of Formula Ia and meta-cresol were varied.

Data Processing. The raw data was normalized to correct for concentration variation in the donor and acceptor well sides. The corrected percents of total were converted to theoretical mM concentrations. These data were then simultaneously fit to the equations presented in the discussion section using Micromath Scientist Software.

B. Preparation of Compounds of Formula I and Ia

In general, the compounds of Formula I and Ia may be prepared by methods that include processes known in the chemical arts, particularly in light of the description contained herein and disclosed in U.S. Pat. Nos. 6,222,038 and 6,255,320. The compounds of Formula I and Ia may be prepared by various different synthetic routes. In particular, the compound of Formula Ia can also be prepared as described in co-pending U.S. provisional application No. 60/541,323, assigned to and owned by Pfizer, Inc. Certain processes for the synthesis of the compound of Formula Ia, as more fully described in the above co-pending provisional application, are illustrated by the following reaction scheme.

The following reaction Scheme illustrates one possible preparation of the citrate monohydrate salt of the compound of Formula Ia, the compound of Formula Ic.

SCHEME I
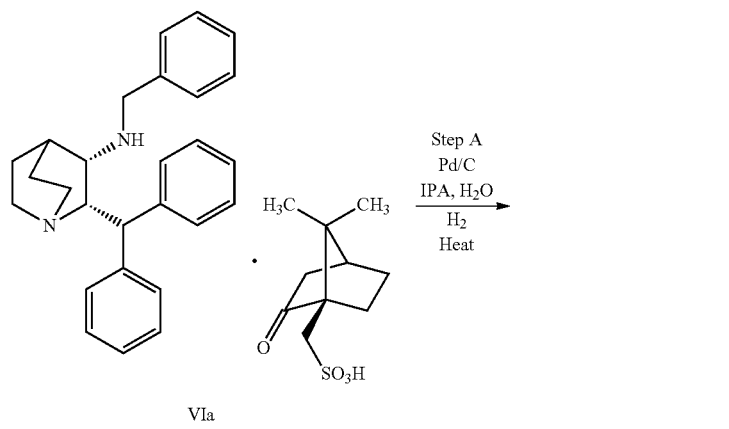
VIa
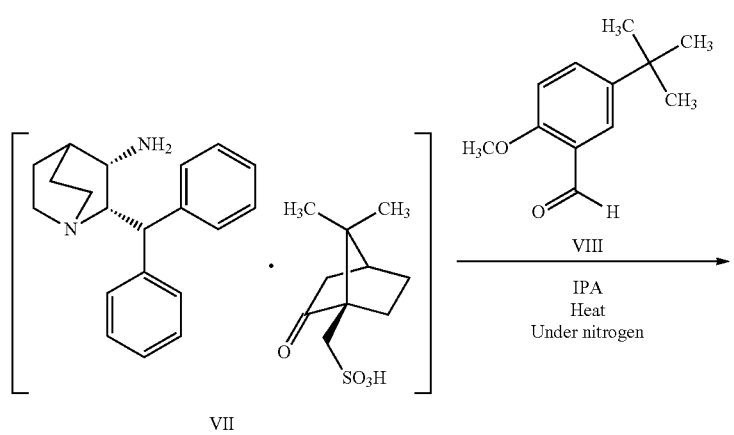
VII
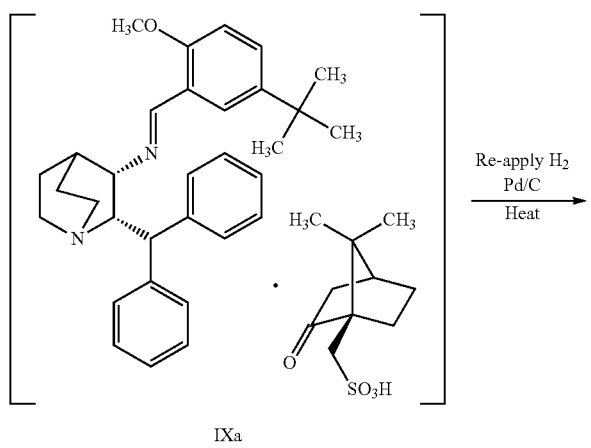
IXa

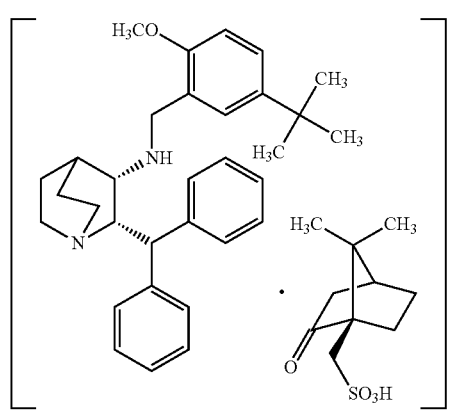

Ib

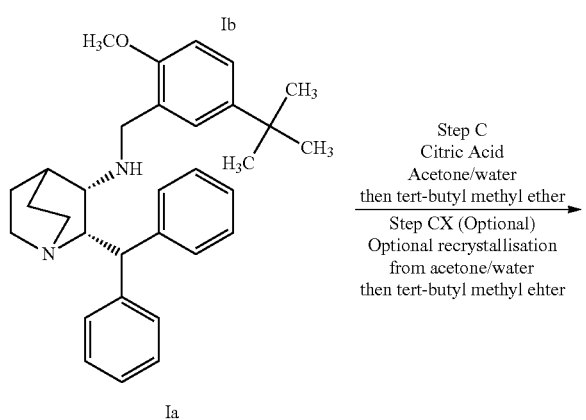

Ia

Step B
1) Toleuene, H₂O, NaOH
2) Concentrate toluene via distillation, displace with propan-2-ol/H₂O
Step BX (Optional)
Optional recrystallisation from propan-2-ol Step C
Citric Acid
Acetone/water
then tert-butyl methyl ether
Step CX (Optional)
Optional recrystallisation from acetone/water
then tert-butyl methyl ehter

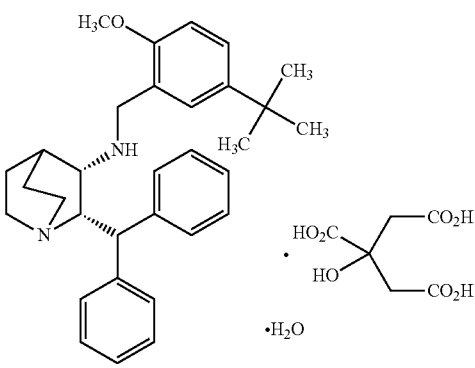

Ic

In Step A of Scheme I, a mixture of compound of Formula VIa in an alcoholic solvent such as methanol, ethanol or n-propanol but preferably propan-2-ol, optionally also in the presence of water, is hydrogenated over a palladium on carbon catalyst at elevated temperature (typically 75-80° C.) and pressure (typically 50 psig hydrogen). One skilled in the art would appreciate that other catalysts may be suitable, such as palladium on carbon, palladium hydroxide on carbon, platinum on carbon, palladium on calcium carbonate, or palladium on alumina ($Al_2O_3$).

Once formation of the intermediate, compound VII, is complete, typically 1 hour, compound of Formula VII, typically as a solution in the respective alcoholic solvent, preferably in propan-2-ol (isopropanol, "IPA") is added to the reaction, without isolating the compound of Formula VIII, and the mixture is stirred optionally at elevated temperature (30-120° C.) under an atmosphere of nitrogen. Once sufficient of the intermediate compound IXa has formed the nitrogen atmosphere is replaced with hydrogen. The reaction is then stirred optionally at elevated temperature (about 30-120° C.) and at elevated pressure (typically 50 psig) until the formation of the compound Ib is found to be complete (typically 18 hours). The reaction mixture is then cooled (about 20-25° C.) and the hydrogen gas is vented. The palladium on carbon catalyst is removed by filtration, and the resultant solution of compound Ib is taken directly into Step B.

In Step B of the reaction scheme I, the solution of compound Ib, typically in a mixture of propan-2-ol and water, is concentrated by distillation followed by the addition of toluene. The mixture is then concentrated again by distillation, adding additional toluene and water as necessary during distillation until sufficient isopropanol had been removed from the mixture and an appropriate solution volume is obtained (typically, 2-4 volumes per kg of compound Ib). Water and toluene are added as necessary (typically about 3.5 volumes of water and about 5 volumes of toluene). One skilled in the art would appreciate that other solvents, other than toluene, such as methylene chloride, ethyl acetate, isopropyl acetate or tert-butyl methyl ether, could be utilized. The pH is adjusted to an appropriate point (about 11.5 to 13.5) by the addition of aqueous sodium hydroxide and if necessary aqueous hydrochloric acid with stirring.

Once an appropriate pH has been obtained, the aqueous phase is removed by separation. The product-containing organic phase is then concentrated by distillation. A mixture of propan-2-ol and water is then added and the mixture is concentrated again by distillation. The addition of water and propan-2-ol and subsequent concentration by distillation is repeated as necessary until sufficient toluene (typically less than 3% w/w toluene by GC analysis) has been removed from the mixture and an appropriate solution volume has been obtained (about 4 volumes with respect to compound Ib), resulting in a composition of the solvent in the final granulation slurry of typically greater than 80% w/w propan-2-ol, less than 20% w/w water and less than 3% w/w toluene.

Once sufficient toluene has been removed, the mixture is cooled until crystallization occurs (typically 70-75° C.). The resultant suspension is then cooled further (typically to 20-25° C.) and is then granulated for a period of time before being optionally cooled further to about 0-5° C. and stirred for a period of time. The solid is then collected by filtration, and the filter cake is washed with propan-2-ol and dried under vacuum at elevated temperature (typically 45-55° C.) to provide compound of formula Ia, as a crystalline solid. One skilled in the art would appreciate that other solvents, other than propan-2-ol, such as methanol, ethanol, n-propanol, acetonitrile, isopropyl acetate, tertiary-amyl alcohol and 4-methyl-2-pentanone could be utilized.

As outlined in the optional Step BX of the reaction scheme, which is not typically required, compound Ib may be further purified. Compound Ib is suspended in propan-2-ol and the mixture is heated at reflux to give a solution. The mixture is then heated at an elevated temperature below the reflux temperature (about 70-75° C.) for about 1 hour during which time crystallization typically occurs. The resultant suspension is maintained at this temperature for a period of about 1 to 2 hours and then cooled (to about 20-25° C.). After stirring at ambient temperature for a period of time (typically 1-18 hours), the solid is collected by filtration. The filter cake is washed with propan-2-ol and then dried under vacuum at elevated temperature (about 45-55° C.) to provide a purified compound Ib, as a crystalline solid. One skilled in the art would appreciate that other solvents, other than propan-2-ol, such as methanol, ethanol, n-propanol, acetonitrile, isopropyl acetate, tertiary-amyl alcohol and 4-methyl-2-pentanone could be utilized.

In Step C of the reaction scheme, compound Ib (1 molar equivalent) and anhydrous citric acid (typically 1.1 molar equivalents) are combined in mixture of acetone (typically about 8-10 volumes) and water (typically about 0.4 volumes), and the resultant solution is filtered. More acetone (typically about 2 volumes) is then added to wash the transfer equipment through. To the filtrate is added a filtered ether solvent such as methyl tertiary-butyl ether (tert-butyl methyl ether, "MTBE") or isopropyl ether ("IPE") (typically about 10 volumes), optionally at elevated temperature (30-45° C.). Once crystallization occurs, which may optionally be initiated by the addition of some seed crystals, the mixture is granulated for a period of time (typically 18 hours), typically at 20-25° C. but optionally at elevated temperature (30-45° C.) for a portion of this time. The solid is then collected by filtration. The filter cake is washed with the respective filtered ether solvent and is then dried at a temperature less than 60° C. (room temperature, if using isopropyl ether) under vacuum optionally with no air or nitrogen bleed to provide compound Ic, the citrate monohydrate, as a crystalline solid. The product may then be optionally milled or sieved.

In optional Step CX, the purity of compound Ic may be improved by dissolving Ic in a mixture of acetone (typically 7 volumes) and water (typically 0.3 volumes) at elevated temperature (about 35-50° C.). The mixture is then cooled (to about 20-35° C.) and optionally filtered. To the resulting mixture is then added a filtered ether solvent, such as tert-butyl methyl ether or isopropyl ether, optionally at elevated temperature (about 30-40° C.). Once crystallization occurs, which may optionally be initiated by the additions of some seed crystals, the mixture is granulated for a period of time (typically 18 hours), typically at 20-25° C. but optionally at elevated temperature (30-45° C.) for a portion of this time. The solid is then collected by filtration. The filter cake is washed with the respective filtered ether solvent and is then dried at a temperature less than 60° C. (room temperature, if using isopropyl ether) under vacuum optionally with no air or nitrogen bleed to provide compound Ic, the citrate monohydrate, as a crystalline solid. The product may then be optionally milled or sieved.

Other pharmaceutically acceptable salts, other than the citrate, may be utilized. For example, malate, maleate, mesylate, lactate, and hydrochloride salts or their in situ equivalents may be prepared by adding equimolar amount of the appropriate acid to the compound Ia, free base solutions.

C. Antimicrobial Preservatives Evaluated for Pharmaceutical Compositions

Table III summarizes the antimicrobial preservatives evaluated for use in the formulation. Each antimicrobial preservative was tested at the highest concentration currently used in commercial products. The antimicrobial preservatives were purchased from general chemical sources.

TABLE III

Antimicrobial Preservatives Screened

| Antimicrobial preservative | Percent (w/v) | pH |
|---|---|---|
| Phenol | 0.5% | 4.4 |
| meta-cresol | 0.3% | 4.4 |
| meta-cresol + EDTA | 0.5% meta-cresol + 0.15% edta | 4.4 |
| Chlorocresol | 0.1% | 4.4 |
| Chlorocresol + EDTA | 0.1% + 0.15% edta | 4.4 |
| Chlorobutanol | 0.5% | 3.5 |
| Chlorobutanol & Phenylethanol | 0.5% each | 3.5 |
| Chlorobutanol & Phenylethanol | 0.5% Chlorbutanol w/Titration of Phenylethanol** | 3.5 |
| Phenylethanol | 0.5% | 3.5 |
| Thimerosal | 0.01% | 4.4 |
| Benzoic Acid | 0.2% | 3.5 |
| Benzethonium chloride | 0.02% | 4.4 |
| Benzalkonium chloride | 0.01% | 4.4 |
| Benzyl alcohol | 2.0% | 4.4 |
| Propylene glycol | 25% | 4.4 |
| Ethanol | 15% | 4.4 |
| Bronopol | 0.1% | 5.0 |
| Sucrose | 50% | 4.4 |
| Chlorhexidine gluconate | 0.5% | 5.0 |

**Titration of Phenylethanol from 0.5-0.1% in 0.1% increments

Preparation of Preserved Formulations. Formulations were prepared, where solubility permitted, at 5% and 10% (weight/volume) SBE-CD. Antimicrobial preservatives with optimal activity at a pH outside the nominal formulation value (pH 4.4) were titrated to either 3.5 or 5.0 using 1 N HCl or 1 N NaOH. A stock solution of either 10% or 5% (weight/volume) SBE-CD containing 10 mgA/mL of the compound of Formula Ia citrate was prepared. Preservative was added to the respective formulation on a weight basis.

Antimicrobial Efficacy Testing. A hybrid USP <24>/Ph. Eur. 2000 antimicrobial effectiveness test (AET) was performed, as follows: 20 mL of drug product was individually inoculated with 0.1-0.2 mL of bacterial or fungal culture, per USP/Ph. Eur. compendial requirements. The final concentration of organisms in the test sample was between $1 \times 10^5$ and $1 \times 10^6$ cfu/mL. At initial 6 hr, 24 hr, 7 day, 14 day, and 28 day time intervals, 1 mL of the inoculated product was transferred into 9 mL of a recovery diluent, that was validated to confirm neutralization of the antimicrobial preservative. One mL of the diluted sample was then transferred to a sterile petri dish and combined with 15-20 mL of an agar broth to culture the organisms. Plates were then incubated for 3 to 5 days, upon which colonies were counted. Initial organism contamination was then calculated based on dilution of the initial sample. Values are reported as "Log Reduction." The organisms used in the AET testing are listed in Table IV.

TABLE IV

Organisms tested in Hybrid (USP/Ph. Eur.) Antimicrobial Efficacy Test

| Test Organism | USP Requirement | Ph. Eur. Requirement |
|---|---|---|
| *Escherichia coli* (bacteria, gram negative) (ATCC 8739) | Yes | Only for oral liquids. |
| *Pseudomonas aeruginosa* (bacteria, gram negative) (ATCC 9027) | Yes | Yes |
| *Staphylococcus aureus* (bacteria, gram positive) (ATCC 6538) | Yes | Yes |
| *Candida albicans* (fungus) (ATCC 10231) | Yes | Yes |
| *Aspergillus niger* (mold) (ATCC 16404) | Yes | Yes |

Generally, the USP test requirements are less stringent than Ph. Eur. requirements, which typically have an immediate bacteriocidal activity requirement. The Ph. Eur. requirements shown in Table III have either a "Criteria A" or "Criteria B" specification depending on the rate of microorganism reduction, with criteria A requiring an increased bacteriocidal rate. In order to meet the combined hybrid assay, the initial inoculum count of microorganisms needed to be reduced by the amounts listed in Table V.

TABLE V

USP/Ph. Eur. Requirements for AET (aqueous parenteral) (Individual USP 24 and Ph. Eur. 2000)

| | Required Log Reduction in Organism Count | | | |
|---|---|---|---|---|
| | Bacteria | | Fungi (Yeasts/Molds) | |
| | USP | Ph. Eur. | USP | Ph. Eur. |
| 6 hr | — | 2 (crit.A) | — | — |
| 24 hr | | 3 (crit. A) 1 (crit. B) | | |
| 7 Day | 1.0 | —(crit. A) 3 (crit. B) | No inc. from initial | 2 (crit. A) |
| 14 day | 3.0 | — | No inc. from initial | 1 (crit. B) |
| 28 day | No increase from 14 day | None recovered (crit. A) No increase (crit. B) | No inc. from initial | No increase |

TABLE V-continued

USP/Ph. Eur. Combined Requirements

| | Required Log Reduction in Organism Count | |
|---|---|---|
| | Bacteria | Fungi (Yeasts/Molds) |
| 6 hr | 2 | — |
| 24 hr | 3 (accept 1, Ph. Eur. B) | — |
| 7 day | 3 | 2 |
| 14 day | 3.0 | 1 |
| 28 day | None recovered | No increase |

Stability Measurements. Potential lead formulations were evaluated under various accelerated stability conditions in order to assess potency and purity of compound of Formula Ia, preservative content and SBE-CD content. For example, in one accelerated stability study, potential lead formulations were placed in stability ovens to measure short-term thermal stability. Sample vials (20 mL) were placed in 70° C., 50° C., 30° C., and 5° C. temperature chambers and analyzed for compound of Formula Ia potency and purity, antimicrobial preservative and SBE-CD content, at 1, 3, 6, and 12-week time intervals. Purity and potency assays to measure compound of Formula Ia, as well as antimicrobial preservatives and SBE-CD content, were performed using validated HPLC methodology. SBE-CD was assayed using GTP 5984.

D. Injection Site Toleration.

Compound of Formula Ia formulations were evaluated for injection site toleration (hereinafter "IST"). In general, formulations not containing SBE-CD were, generally, poorly tolerated. Formulations consisting of 10 mgA/mL compound of Formula Ia, 10% excess meta-cresol (0.33% w/v) and about 6.8% to 7.6% SBE-CD were evaluated for IST. In particular, formulations containing 10 mgA/mL compound of Formula Ia, 61 to 72 mg/mL SBE-CD and 3.2 to 4.2 mg/mL meta-cresol were tested for injection site toleration and all were well tolerated.

Formulations were tested in groups of 4 dogs comprised of beagles and mongrels. On each of four consecutive days, the dogs daily received two subcutaneous injections of vehicle alone as a control over the left shoulder at 0.1 ml/kg and active formulation (10 mgA/mL compound of Formula Ia at 1 mg/kg) over the right shoulder. Dogs were observed daily for evidence of reaction at the injection site and a score of 0-4 (see Table VI) was given for each of the following parameters: pain on injection, erythema, tissue thickening, pain on palpation and edema. Dogs were observed daily until day 5 (24 hours after the last dose).

TABLE VI

Injection Site Toleration Scoring

| Pain on Injection | Erythema | Tissue Thickening | Pain on Palpation | Edema |
|---|---|---|---|---|
| 0 = no reaction | 0 = no erythema | 0 = no thickening | 0 = no pain | 0 = no edema |
| 1 = very slight response hunch, look @ site | 1 = very slight erythema barely perceptible | 1 = very slight reaction barely perceptible | 1 = mild pain on deep palpation | 1 = very mild edema barely perceptible |
| 2 = mild response minor vocalization lick/scratch @ site | 2 = mild erythema well defined | 2 = mild, palpable reaction <= 1 cm | 2 = mild pain on palpation | 2 = mild palpable edema |
| 3 = moderate response major vocalization bite @ site, motor activity | 3 = moderate erythema reaction 1-2 cm | 3 = moderate, palpable on palpation | 3 = moderate pain | 3 = moderate palpable focal edema |

TABLE VI-continued

Injection Site Toleration Scoring

| Pain on Injection | Erythema | Tissue Thickening | Pain on Palpation | Edema |
|---|---|---|---|---|
| 4 = severe response similar to 3, >5 min duration | 4 = severe erythema beet redness any eschar formation | 4 = severe reaction >2 cm | 4 = severe pain on palpation | 4 = severe diffuse edema |

EXPERIMENTALS

Experimental 1

Selection of Antimicrobial Preservatives for Injectable Compound of Formula Ia

Study A (Large Antimicrobial Preservative Screen)

The efficacy of several different antimicrobial preservatives in combination with compound of Formula Ia and SBE-CD were investigated. Literature indicated that the antimicrobial preservatives that met both the USP and either Ph. Eur. criteria A or B requirements were ethanol, propylene glycol, benzoic acid, thimerosal, meta-cresol, (Lucchini, J. J.; Corre, J.; and Cremieux, A. "Antibacterial activity of phenolic compounds and aromatic alcohols" *Res. Microbiol.* 141, 499-510, (1990)) and the combination of chlorobutanol/phenylethanol.

Table VII sets forth results for screening various antimicrobial preservatives or combinations thereof.

TABLE VII

ANTIMICROBIAL EFFECTIVENESS TESTING:
SCREEN FOR ANTIMICROBIAL PRESERVATIVE SYSTEM

| | | | AET RESULTS AGAINST COMPENDIA | | |
|---|---|---|---|---|---|
| ANTIMICROBIAL PRESERVATIVE | FORMULATION DESCRIPTION | ACCEPTABLE STABILITY | USP | Ph. Eur. Criteria A | Ph. Eur. Criteria B |
| Benzalkonium Chloride (0.01%) | pH 4.4 10% SBE-CD | Not Tested | | | |
| Benzalkonium Chloride (0.01%) | pH 4.4 5% SBE-CD | Not Tested | ✓ | | |
| Benzalkonium Chloride (0.02%) | pH 4.4 5% SBE-CD | Not Tested | | | |
| Benzethonium Chloride (0.02%) | pH 4.4 10% SBE-CD | Not Tested | | | |
| Benzethonium Chloride (0.02%) | pH 4.4 5% SBE-CD | Not Tested | ✓ | | |
| Benzethonium Chloride (0.04%) | pH 4.4 5% SBE-CD | Not Tested | | | |
| Benzoic Acid (0.2%) | pH 4.2 5% SBE-CD | Not Tested | ✓ | | ✓ |
| Benzoic Acid (0.2%) | pH 4.2 10% SBE-CD | ✓ | ✓ | | |
| Bronopol (0.1%) | pH 5.0 10% SBE-CD | Not Tested | ✓ | | |
| Bronopol (0.1%) | pH 5.0 5% SBE-CD | Not Tested | ✓ | | ✓ |
| Bronopol (0.2%) | pH 5.0 5% SBE-CD | Not Tested | ✓ | | ✓ |
| Chlorobutanol (0.5%) | pH 3.5 5% SBE-CD | Not Tested | ✓ | | |
| Chlorobutanol & Phenylethanol (0.5%/0.5%) | pH 3.5 5% SBE-CD | Not Tested | ✓ | ✓ | ✓ |
| Chlorobutanol & Phenylethanol (0.5%/0.5%) | pH 3.5 10% SBE-CD | ✓ | | | |
| Chlorobutanol & Phenylethanol (0.5%/0.4%) | pH 3.5 10% SBE-CD | Not Tested | | | |
| Chlorobutanol & Phenylethanol (0.5%/0.3%) | pH 3.5 10% SBE-CD | Not Tested | | | |
| Chlorobutanol & Phenylethanol (0.5%/0.2%) | pH 3.5 10% SBE-CD | Not Tested | | | |
| Chlorobutanol & Phenylethanol (0.5%/0.1%) | pH 3.5 10% SBE-CD | Not Tested | | | |
| Chlorhexidine Gluconate (0.5%) | pH 5.0 5% SBE-CD | Not Tested | ✓ | | |

TABLE VII-continued

ANTIMICROBIAL EFFECTIVENESS TESTING:
SCREEN FOR ANTIMICROBIAL PRESERVATIVE SYSTEM

| ANTIMICROBIAL PRESERVATIVE | FORMULATION DESCRIPTION | ACCEPTABLE STABILITY | AET RESULTS AGAINST COMPENDIA | | |
|---|---|---|---|---|---|
| | | | USP | Ph. Eur. Criteria A | Ph. Eur. Criteria B |
| Ethanol (15%) | pH 4.4 10% SBE-CD | Not Tested | ✓ | | ✓ |
| Ethanol (15%) | pH 4.4 5% SBE-CD | ✓ | ✓ | | ✓ |
| Ethanol (30%) | pH 4.4 5% SBE-CD | Not Tested | ✓ | ✓ | ✓ |
| Benzalkonium Chloride (0.01%) | pH 4.4 10% SBE-CD | Not Tested | | | |
| Benzalkonium Chloride 0.01% | pH 4.4 5% SBE-CD | Not Tested | ✓ | | |
| Benzalkonium Chloride (0.02%) | pH 4.4 5% SBE-CD | Not Tested | | | |
| Benzethonium Chloride (0.02%) | pH 4.4 10% SBE-CD | Not Tested | ✓ | | |
| Benzethonium Chloride (0.02%) | pH 4.4 5% SBE-CD | Not Tested | | | |
| Benzethonium Chloride (0.04%) | pH 4.4 5% SBE-CD | Not Tested | | | |
| Benzoic Acid (0.2%) | pH 4.2 5% SBE-CD | Not Tested | ✓ | | ✓ |
| Benzoic Acid (0.2%) | pH 4.2 10% SBE-CD | ✓ | ✓ | | |
| Bronopol (0.1%) | pH 5.0 10% SBE-CD | Not Tested | ✓ | | |
| Bronopol (0.1%) | pH 5.0 5% SBE-CD | Not Tested | ✓ | | ✓ |
| Bronopol (0.2%) | pH 5.0 5% SBE-CD | Not Tested | ✓ | | ✓ |
| Chlorobutanol (0.5%) | pH 3.5 5% SBE-CD | Not Tested | ✓ | | |
| Chlorobutanol & Phenylethanol (0.5%/0.5%) | pH 3.5 5% SBE-CD | Not Tested | ✓ | ✓ | ✓ |
| Chlorobutanol & Phenylethanol (0.5%/0.5%) | pH 3.5 10% SBE-CD | ✓ | | | |
| Chlorobutanol & Phenylethanol (0.5%/0.4%) | pH 3.5 10% SBE-CD | Not Tested | | | |
| Chlorobutanol & Phenylethanol (0.5%/0.3%) | pH 3.5 10% SBE-CD | Not Tested | | | |
| Chlorobutanol & Phenylethanol (0.5%/0.2%) | pH 3.5 10% SBE-CD | Not Tested | | | |
| Chlorobutanol & Phenylethanol (0.5%/0.1%) | pH 3.5 10% SBE-CD | Not Tested | | | |
| Chlorhexidine Gluconate (0.5%) | pH 5.0 5% SBE-CD | Not Tested | ✓ | | |
| Ethanol (15%) | pH 4.4 10% SBE-CD | Not Tested | ✓ | | ✓ |
| Ethanol (15%) | pH 4.4 5% SBE-CD | ✓ | ✓ | | ✓ |
| Ethanol (30%) | pH 4.4 5% SBE-CD | Not Tested | ✓ | ✓ | ✓ |
| meta-cresol (0.3%) | pH 4.4 10% SBE-CD | ✓ | ✓ | | |
| meta-cresol (0.3%) | pH 4.4 8% SBE-CD | Not Tested | ✓ | | ✓ |
| meta-cresol (0.3%) | pH 4.4 9% SBE-CD | Not Tested | ✓ | | ✓ |
| Phenol (0.5%) | pH 4.4 10% SBE-CD | ✓ | ✓ | | ✓ |
| Phenylethanol (0.5%) | pH 3.5 10% SBE-CD | Not Tested | | | |
| Propylene Glycol (25%) | pH 4.4 10% SBE-CD | Not Tested | ✓ | | |
| Propylene Glycol (25%) | pH 4.4 5% SBE-CD | Not Tested | ✓ | | |
| Propylene Glycol (50%) | pH 4.4 5% SBE-CD | Not Tested | ✓ | ✓ | ✓ |

TABLE VII-continued

ANTIMICROBIAL EFFECTIVENESS TESTING:
SCREEN FOR ANTIMICROBIAL PRESERVATIVE SYSTEM

| ANTIMICROBIAL PRESERVATIVE | FORMULATION DESCRIPTION | ACCEPTABLE STABILITY | AET RESULTS AGAINST COMPENDIA | | |
|---|---|---|---|---|---|
| | | | USP | Ph. Eur. Criteria A | Ph. Eur. Criteria B |
| Sucrose (50%) | pH 4.4 5% SBE-CD | Not Tested | | | |
| Thimerosal (0.02%) | pH 4.4 10% SBE-CD | Not Tested | ✓ | ✓ | ✓ |
| Thimerosal (0.01%) | pH 4.4 10% SBE-CD | Poor Stability | ✓ | ✓ | ✓ |
| Thimerosal (0.01%) | pH 4.4 5% SBE-CD | Not Tested | ✓ | ✓ | ✓ |
| Thimerosal (0.02%) | pH 4.4 5% SBE-CD | Not Tested | ✓ | ✓ | ✓ |

✓ denotes USP and/or Ph. Eur. Criteria satisfied

Formulations containing these antimicrobial preservatives were further evaluated for physical and chemical stability and injection site toleration. (See Table VII). The co-solvent antimicrobial preservative approaches, ethanol and propylene glycol, failed to satisfy acceptable IST. Furthermore, benzoic acid formulations also provided poor IST results.

TABLE VIII

Results of Study A

| Antimicrobial preservative Formulation* | Antimicrobial preservative Content (Actual/ Precedence) | IST | Stability | AET Results | | |
|---|---|---|---|---|---|---|
| | | | | USP | Ph. Eur. Criteria A | Ph. Eur. Criteria B |
| Benzoic acid pH: 4.2 SBE-CD: 10% | 0.2%/0.2% | Poor | OK 12 w/70 C. | ✓ | s. aur (6, 24 hr) c. alb (7 d) | ✓ |
| Chlorobutanol & Phenylethanol pH: 3.5 SBE-CD: 5% | 05%/05% Chloro/Phenyl | Poor | NT | ✓ | ✓ | ✓ |
| Ethanol pH: 4.4 SBE-CD: 10% | 15%/70% | Poor | NT | ✓ | s. aur (6 hr) | ✓ |
| Ethanol pH: 4.4 SBE-CD: 5% | 15%/70% | Poor | OK 1 w/70 | ✓ | a. niger (7 d) | ✓ |
| meta-cresol pH: 4.4 SBE-CD: 10% | 0.3%/0.3% | Good | OK 12 w/70 C. | ✓ | s. aur (6, 24 hr) c. alb (7 d) | ✓ |
| Propylene glycol pH: 4.4 SBE-CD: 10% | 50%/40% | Poor | NT | ✓ | ✓ | ✓ |
| Thimerosal pH: 4.4 SBE-CD: 10% | 0.01/0.01% | Good | 1 wk/70 | ✓ | ✓ | ✓ |

*All formulations contained compound of Formula Ia at 10 mgA/mL

✓ denotes USP and/or Ph. Eur. Criteria satisfied.

Study B (Ph. Eur. Criteria B Meeting Antimicrobial Preservative Screen)

All antimicrobial preservatives that met Ph. Eur. criteria B were further screened for injection site toleration and stability. The leads identified in Table VII and Table IX that met criteria B were thimerosal, meta-cresol, and benzoic acid. These formulations were evaluated for stability and IST (Table VII).

Results from the studies indicated that stability of thimerosal was commercially undesirable for the formulation. Only 30% of the thimerosal remained in the formulation after 1 week at 70° C. storage and complete loss was observed after 6 weeks. (Tan, M., Parkin, L. E. "Route of decomposition of thimerosal" *Int. J. Pharm.* 195 No. 1-2, 23-34, 2000).

Benzoic acid showed no detectable loss over 12 weeks at 70° C. storage, which was sufficiently stable for the formulation. Although the stability of benzoic acid was acceptable, moderate to severe pain on injection eliminated it from further consideration.

On the other hand, meta-cresol containing formulations exhibited excellent stability and injection site toleration. Accordingly, meta-cresol was identified as the preferable antimicrobial preservative due to excellent injection site tolerability, as well as robustly meeting Ph. Eur. criteria A for preservative efficacy. Because of these favorable performance characteristics, the formulation was optimized with respect to SBE-CD concentration, resulting in a formulation with a high margin of solubility, robust antimicrobial preservative efficacy, and acceptable injection site toleration.

The stability of meta-cresol and compound of Formula Ia in formulations containing 3 mg/mL meta-cresol, 100 mg/mL SBE-CD and 10 mgA/mL compound of Formula Ia is shown in Table IX. Robust stability for both compound of Formula Ia and meta-cresol was demonstrated. The compound of Formula Ia experienced a 3% loss (relative to 1 week at 5° C.) after 12 weeks at 70° C., while the meta-cresol potency decreased by 2%.

TABLE IX

Stability of meta-cresol and compound of Formula Ia

| Storage Condition | Time-point | Compound of Formula Ia CONTENT (% INTENT) | | meta-cresol CONTENT (% INTENT) | |
|---|---|---|---|---|---|
| | | Amber-Treated | Amber-Untreated | Amber-Treated | Amber-Untreated |
| 70° C. | 1 week | 94 | 94 | 100 | 100 |
| | 2 weeks | 94 | 94 | 103 | 103 |
| | 3 weeks | 92 | 94 | 100 | 102 |
| | 6 weeks | 92 | 93 | 101 | 101 |
| | 12 weeks | 93 | 93 | 100 | 100 |
| 50° C. | 1 week | 95 | 96 | 99 | 100 |
| | 3 weeks | 95 | 93 | 103 | 101 |
| | 6 weeks | 96 | 94 | 104 | 102 |
| | 12 weeks | 95 | Not tested | 100 | Not tested |
| 5° C. | 1 week | 97 | 96 | 102 | 102 |
| | 3 weeks | 96 | 95 | 104 | 103 |
| | 6 weeks | 95 | 94 | 104 | 102 |
| | 12 weeks | 94 | 94 | 98 | 98 |
| ICH Photostability | 1X ICH UV/FI | 92 | 93 | 102 | 102 |

Preferred Embodiments

A. A pharmaceutical composition comprising a therapeutically effective amount of an Active Pharmaceutical Ingredient, a β-cyclodextrin, a pharmaceutically acceptable preservative, a pharmaceutically acceptable vehicle, and an optional pharmaceutically acceptable excipient, wherein the preservative demonstrates pharmaceutically acceptable antimicrobial preservative effectiveness.

B. The pharmaceutical composition according to preferred embodiment A wherein the β-cyclodextrin is 2-hydroxypropyl-β-cyclodextrin or sulfobutyl ether-β-cyclodextrin.

C. The pharmaceutical composition according to preferred embodiment B wherein the preservative is selected from thimerosal, propylene glycol, phenol, or meta-cresol or a combination thereof.

D. The pharmaceutical composition according to preferred embodiments B or C wherein the preservative has a binding value to the cyclodextrin that is less than a binding value of the Active Pharmaceutical Ingredient to cyclodextrin.

E. The pharmaceutical composition according to preferred embodiment D, wherein the concentration of preservative is about 0.1 mg/mL to about 600 mg/mL.

F. The pharmaceutical composition according to preferred embodiment E, wherein the preservative is meta-cresol and the concentration of preservative is about 0.1 mg/mL to about 20 mg/mL.

G. The pharmaceutical composition according to preferred embodiment F wherein about 1 mg/mL to about 5 mg/mL of the meta-cresol is unsequestered in the cyclodextrin.

H. The pharmaceutical composition according to preferred embodiment G wherein about 2.5 mg/mL of the preservative is unsequestered in the cyclodextrin.

I. The pharmaceutical composition according to preferred embodiment D wherein the binding value of the Active Pharmaceutical Ingredient to cyclodextrin is between 500 $M^{-1}$ and 10,000 $M^{-1}$.

J. The pharmaceutical composition according to preferred embodiment I wherein the binding value of the Active Pharmaceutical Ingredient to cyclodextrin is between 800 $M^{-1}$ and 3,000 $M^{-1}$.

K. The pharmaceutical composition according to preferred embodiment D wherein the Active Pharmaceutical Ingredient has a greater than or equal to two-fold binding constant with cyclodextrin over that of the preservative.

L. The pharmaceutical composition according to preferred embodiment K wherein the binding constant is greater than or equal to five-fold.

M. The pharmaceutical composition according to preferred embodiment L wherein the binding constant is greater than or equal to ten-fold.

N. The pharmaceutical composition according to preferred embodiment D having antimicrobial effectiveness against bacteria such that the bacteria concentration decreases at a 2 or greater log reduction after 6 hours, a 3 or greater log reduction after 24 hours, and zero recovery of bacteria after 28 days.

O. The pharmaceutical composition according to preferred embodiment N wherein the bacteria are *Escherichia coli* (bacteria, gram negative)(ATCC8739), *Pseudomonas aeruginosa* (bacteria, gram negative)(ATCC9027) and *Staphylococcus auereus* (bacteria, gram positive)(ATCC6538).

P. The pharmaceutical composition according to preferred embodiment O having antimicrobial effectiveness against a fungus or mold such that the fungus or mold concentration decreases at a 2 or greater log reduction after 7 days, a 1 log reduction after 14 days, and no increase in fungus or mold after 14 days to about 28 days.

Q. The pharmaceutical composition according to preferred embodiment P wherein the fungus is *Candida albicans* (fungus)(ATCC 10231).

R. The pharmaceutical composition according to preferred embodiment P wherein the mold is *Aspergillus niger* (mold) (ATCC 16404).

S. A pharmaceutical composition of preferred embodiment D wherein the antimicrobial effectiveness satisfies Ph. Eur. Criteria A and B and USP AET criteria.

T. A pharmaceutical composition comprising a compound of Formula I,

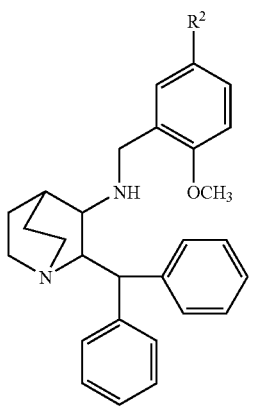

wherein R² is selected from the group consisting of methyl, ethyl, isopropyl, sec-butyl and tertbutyl, a pharmaceutically acceptable β-cyclodextrin, a pharmaceutically acceptable preservative, a pharmaceutically acceptable vehicle and an optional pharmaceutically acceptable excipient.

U. The pharmaceutical composition according to preferred embodiment T wherein the β-cyclodextrin is 2-hydroxypropyl-β-cyclodextrin or sulfobutyl ether-⊕-cyclodextrin.

V. The pharmaceutical composition according to preferred embodiment U wherein the pharmaceutically acceptable preservative is selected from thimerosal, propylene glycol, phenol or meta-cresol, or a combination thereof.

W. The pharmaceutical composition according to preferred embodiment V wherein the preservative is meta-cresol.

X. The pharmaceutical composition according to preferred embodiment W having a pH in a range of about 4 to about 5.

Y. The pharmaceutical composition according to preferred embodiments W or X wherein about 1 mg/mL to about 5 mg/mL of the preservative is unsequestered in the cyclodextrin.

Z. The pharmaceutical composition according to preferred embodiment Y wherein the compound of Formula I, or a pharmaceutically acceptable salt thereof, is in an amount of about 0.1 mg/mL to about 100 mg/mL and the β-cyclodextrin is in an amount of about 20 mg/mL to about 200 mg/mL and the preservative is meta-cresol.

A1. A pharmaceutical composition according to preferred embodiment Z wherein the β-cyclodextrin is in the amount of 55 mg/mL to 100 mg/mL and the meta-cresol is an amount of about 2.5 mg/mL to 3.5 mg/mL.

B1. A pharmaceutical composition according to preferred embodiments T, U, W or X wherein the compound of Formula I is the compound of Formula Ia,

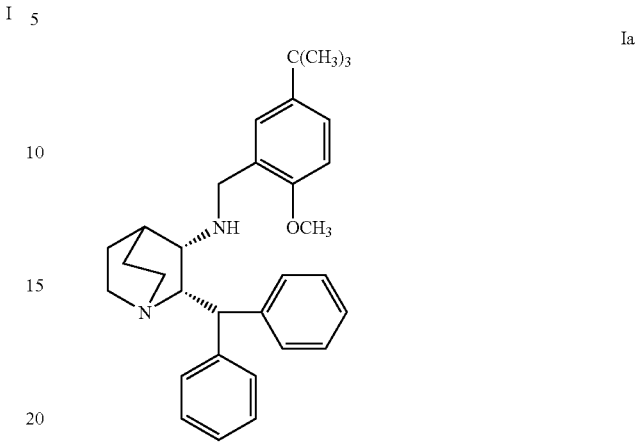

or its pharmaceutically acceptable salts.

C1. A pharmaceutical composition according to preferred embodiment B1 wherein the compound of Formula Ia, or a pharmaceutically acceptable salt thereof, is in an amount of about 0.1 mg/mL to about 100 mg/mL and the β-cyclodextrin is in an amount of about 20 mg/mL to about 200 mg/mL and the preservative is meta-cresol and is in an amount of about 1 mg/mL to about 5 mg/mL.

D1. The pharmaceutical composition according to preferred embodiment C1 wherein the β-cyclodextrin is in an amount of about 55 mg/mL to about 100 mg/mL and the preservative is meta-cresol and is in an amount of about 2.5 mg/mL to about 3.5 mg/mL.

E1. The pharmaceutical composition according to preferred embodiment D1 wherein the β-cyclodextrin is sulfobutyl ether-β-cyclodextrin.

F1. A pharmaceutical composition comprising the compound of Formula Ia,

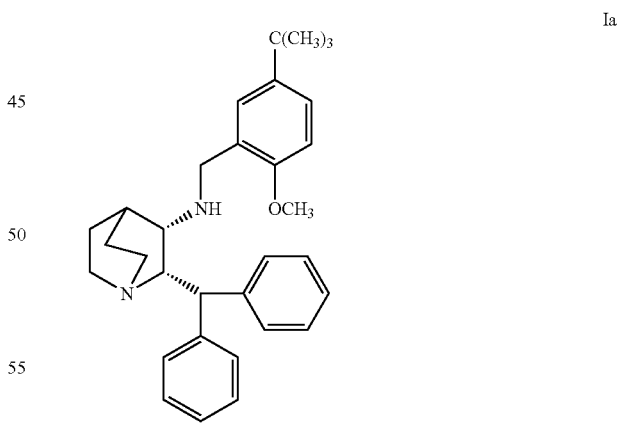

or its pharmaceutically acceptable salts, wherein the compound of Formula Ia is 10 mgA/mL, sulfobutyl ether-β-cyclodextrin is in an amount of about 63 mg/mL and meta-cresol is in an amount of about 3.3 mg/mL, a pharmaceutically acceptable vehicle and an optional pharmaceutically acceptable excipient.

G1. The pharmaceutical composition of preferred embodiment F1 wherein the pharmaceutically acceptable salt of the compound of Formula Ia is citrate.

H1. A method for the treatment of emesis or improving anesthesia recovery in mammals comprising parenterally injecting into the mammal an aqueous pharmaceutical composition comprising the pharmaceutical composition of preferred embodiments T, U, V, W, X, F1 or G1, the β-cyclodextrin being present in amounts which are sufficient for improved injection toleration at the injection site.

I1. A method for the treatment of emesis or improving anesthesia recovery in mammals comprising parenterally injecting into the mammal an aqueous pharmaceutical composition comprising the pharmaceutical composition of preferred embodiment F1.

J1. The method according to preferred embodiment I1 wherein the pharmaceutically acceptable salt is citrate.

K1. The method according to preferred embodiments I1 or J1 wherein administration is subcutaneous.

L1. A method of improving injection site toleration during the treatment of emesis or the treatment of improving anesthesia recovery in a mammal comprising parenterally injecting into the mammal a pharmaceutically acceptable solution of the the pharmaceutical composition according to preferred embodiments T, U, V, W, X, F1 or G1.

M1. A method of improving injection site toleration during the treatment of emesis or the treatment of improving anesthesia recovery in a mammal comprising parenterally injecting into the mammal a pharmaceutically acceptable solution of the the pharmaceutical composition according to preferred embodiment F1.

N1. The method of preferred embodiment M1 wherein the pharmaceutically acceptable salt is citrate.

O1. A method to develop preserved API compositions comprising a therapeutically effective amount of an API, a β-cyclodextrin and a pharmaceutically acceptable preservative.

P1. The method according to preferred embodiment O1 wherein the preservative has a binding value to the cyclodextrin that is less than a binding value of the API to cyclodextrin.

Q1. The method according to preferred embodiment P1 wherein the preservative is selected from thimerosal, glycol, phenol or meta-cresol or a combination thereof R1. The method of preferred embodiments P1 or Q1 wherein the binding value of the API with the cyclodextrin is greater than 50 $M^{-1}$.

S1. The method of preferred embodiment R1 wherein the binding value of the API with the cyclodextrin is between 500 and 10,000 $M^{-1}$.

T1. The method of preferred embodiment S1 wherein the binding value of the API with the cyclodextrin is between 800 and 3,000 $M^-$.

U1. The method of preferred embodiment T1 wherein Antimicrobial Effectiveness Test (AET) requirements meet Pharmaceopia Europa Criteria A and B and USP AET criteria.

The invention claimed is:

1. A parenteral pharmaceutical composition with injection site toleration comprising a therapeutically effective amount of a compound of Formula (1a),

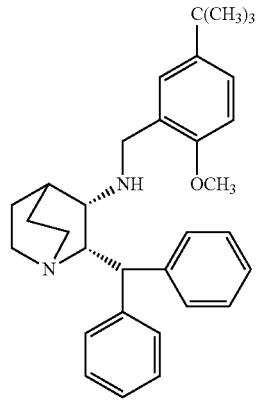

(Ia)

or a pharmaceutically acceptable salt thereof, a β-cyclodextrin, a pharmaceutically acceptable preservative, a pharmaceutically acceptable vehicle, and an optional pharmaceutically acceptable excipient, wherein the preservative demonstrates pharmaceutically acceptable antimicrobial preservative effectiveness and is selected from the group consisting of thimerosal, propylene glycol, phenol, or meta-cresol.

2. The pharmaceutical composition according to claim 1 wherein the β-cyclodextrin is 2-hydroxypropyl-β-cyclodextrin or sulfobutyl ether-β-cyclodextrin.

3. The pharmaceutical composition according to claim 2 wherein the preservative is about 2.5 to about 3.5 mg/mL of meta-cresol, the cyclodextrin is sulfobutyl ether-β-cyclodextrin, and wherein the pharmaceutically acceptable salt is the citrate monohydrate salt.

4. The pharmaceutical composition according to claim 3 wherein the preservative has a binding value to the cyclodextrin that is less than the binding value of the compound of Formula (1a) to cyclodextrin.

5. The pharmaceutical composition according to claim 4 wherein the binding value of the compound of Formula (1a) to cyclodextrin is between 800 $M^{-1}$ and 3,000 M.

6. A pharmaceutical composition comprising about 10 mg/mL of a compound of Formula (1a),

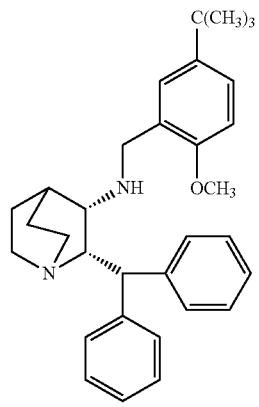

(Ia)

about 3.3 mg/mL meta-cresol, about 63 mg/mL sulfobutyl ether-β-cyclodextrin, and a pharmaceutically acceptable vehicle.

7. A method for the treatment of emesis in an animal comprising administering to said animal a composition according to claim 1.

* * * * *

UNITED STATES PATENT AND TRADEMARK OFFICE
CERTIFICATE OF CORRECTION

PATENT NO.        : 8,183,230 B2
APPLICATION NO.   : 10/588070
DATED             : May 22, 2012
INVENTOR(S)       : Adami et al.

It is certified that error appears in the above-identified patent and that said Letters Patent is hereby corrected as shown below:

Column 36, line 41, at the end of the line, "3000 M." should read "3000 M-1."

Signed and Sealed this
Twenty-eighth Day of August, 2012

David J. Kappos
*Director of the United States Patent and Trademark Office*